United States Patent [19]

Botstein et al.

[11] Patent Number: 5,677,153
[45] Date of Patent: Oct. 14, 1997

[54] METHODS FOR MODIFYING DNA AND FOR DETECTING EFFECTS OF SUCH MODIFICATION ON INTERACTION OF ENCODED MODIFIED POLYPEPTIDES WITH TARGET SUBSTRATES

[75] Inventors: David Botstein, Belmont; Timothy Palzkill, Union City, both of Calif.

[73] Assignee: Genentech, Inc., South San Francisco, Calif.

[21] Appl. No.: 346,333

[22] Filed: Nov. 29, 1994

Related U.S. Application Data

[63] Continuation of Ser. No. 39,501, Mar. 29, 1993, abandoned, which is a continuation of Ser. No. 602,158, Oct. 22, 1990, abandoned.

[51] Int. Cl.$^6$ .................................................. C12N 15/64
[52] U.S. Cl. .................. 435/91.4; 435/91.2; 435/91.41; 435/91.42
[58] Field of Search .............................. 435/6, 91.2, 91.4, 435/91.41, 91.42

[56] References Cited

U.S. PATENT DOCUMENTS

| | | | |
|---|---|---|---|
| 4,643,969 | 2/1987 | Inouye et al. | 435/68 |
| 4,683,202 | 7/1987 | Mullis | 435/91 |
| 4,769,326 | 9/1988 | Rutter | 435/68 |
| 4,935,357 | 6/1990 | Szybalski | 435/91 |

OTHER PUBLICATIONS

Russell et al. J. Mol. Biol. 244 332–350 Structural features can be unconserved in proteins with similar folds.
Dube, et al., *Biochemistry*, vol. 28, No. 14, 5704–5707, Jul. 11, 1989.
Mormeneo, et al., *Gene*, 61 (1987) 21–30.
Ghrayeb, J., et al., "Secretion cloning vectors in *Escherichia coli*", *The EMBO Journal*, 3:2437–2442 (1984).
Kaiser, C. A., et al., "Many Random Sequences Functionally Replace the Secretion Signal Sequence of Yeast Invertase", *Science*, 235:312–317 (1987).
Reidhaar–Olson, J. F., et al., "Functionally Acceptable Substitutions in Two α–Helical Regions of λ Repressor", *Proteins: Structure, Function and Genetics*, 7:306–316 (1990).
Dube D.K., et al. "Mutants Generated by the Insertion of Random Oligonucleotides into the Active Site of the β–Lactamase Gene", *Biochemistry*, 28:5703–5707 (1989).
Heffron, F., et al., "In vitro mutagenesis of a circular DNA molecule by using synthetic restriction sites", *Proc. Natl. Acad. Sci. USA*, 75:6012–6016 (1978).
McKnight, S. L., et al., "Transcriptional Control Signals of a Eukaryotic Protein–Coding Gene", *Science*, 217:316–324 (1982).
Mormeneo, S., et al., "Precise nucleotide sequence modifications with bidirectionally cleaving class–IIS excision linkers", *Gene*, 61:21–30 (1987).
Szybalski, W., "Universal restriction endonucleases: designing novel cleavage specificities by combining adapter oligodeoxynucleotide and enzyme moieties", *Gene*, 40:169–173 (1985).

*Primary Examiner*—Mindy Fleisher
*Assistant Examiner*—John S. Brusca
*Attorney, Agent, or Firm*—Richard F. Trecartin; Flehr, Hohbach, Test, Albritton & Herbert

[57] ABSTRACT

The invention relates to methods and mutation linkers to modify DNA, to methods for producing libraries containing a multiplicity of modified DNA, and to methods for using such libraries for screening modified proteins encoded by such DNA. The DNA targeted for modification typically encodes a polypeptide such as an enzyme. The libraries are used to determine the effect of such modification or the interaction of the modified polypeptides with a target. In preferred embodiments, the invention relates to methods for making and using libraries containing DNA encoding modified antibiotic hydrolases to screen antibiotics against one or more of the modified antibiotic hydrolases produced by such libraries. Susceptibility or lack of susceptibility of an antibiotic to neutralization provides an indication of whether wild-type antibiotic hydrolases are likely to mutate to confer resistance to the antibiotic.

40 Claims, 23 Drawing Sheets

FIG._1A
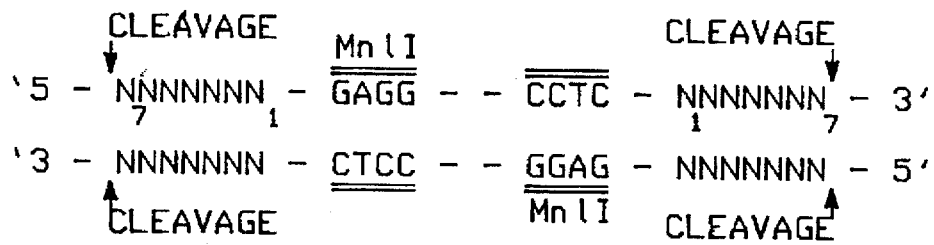
FIG._1B
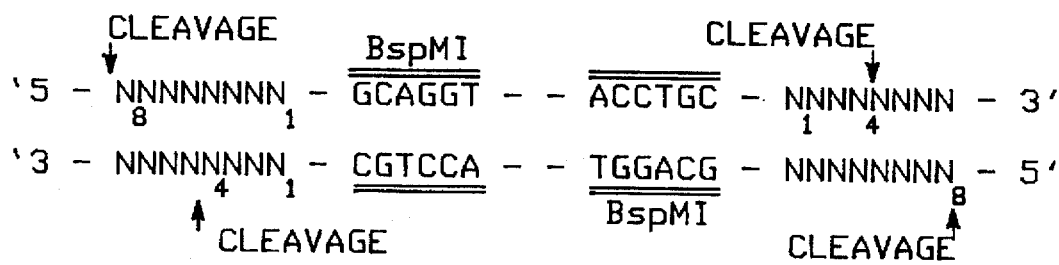
FIG._1
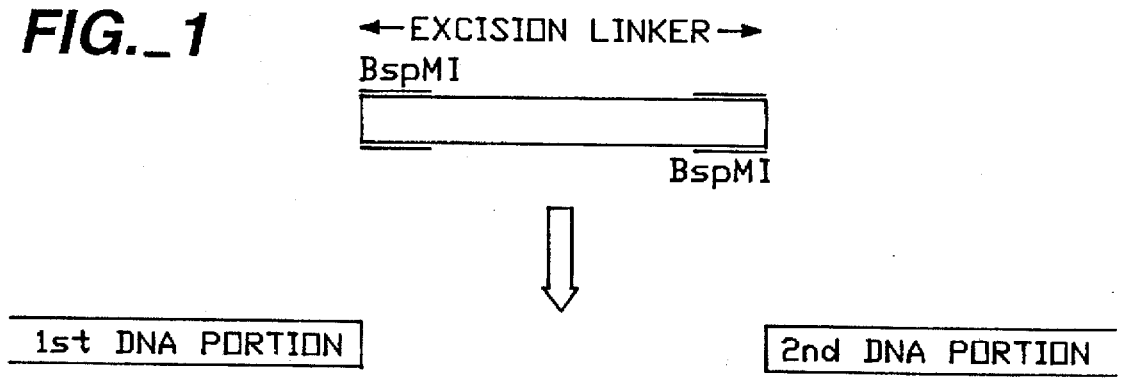
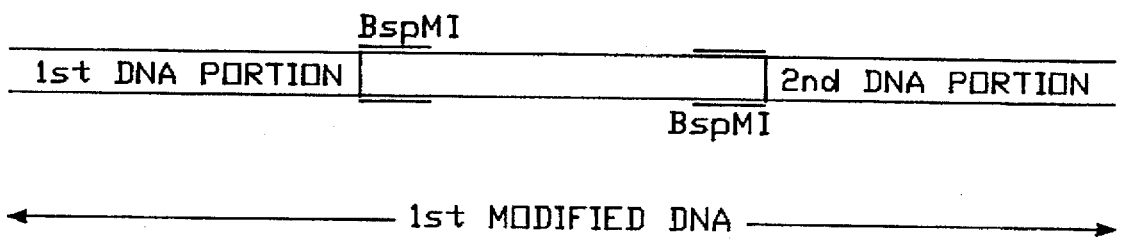

FIG._2

R = RECOGNITION SEQUENCE FOR CLASS IIS RESTRICTION ENDONUCLEASE.

TNER = TARGET NUCLEOTIDE END REGION.

$N_X$ = # NUCLEOTIDES DISTANT FROM R TO POINT IN TARGET WHERE DNA CLASS IIS CLEAVES.

MNER = MUTATION NUCLEOTIDE END REGION.

$M_X$ = # NUCLEOTIDES DESTINED FOR INCLUSION IN TARGET DNA.

$S_X$ = # NUCLEOTIDES DISTANT FROM R TO POINT IN MUTATION LINKERS WHERE CLASS IIS CLEAVES.

FIG._2A
TARGET DNA
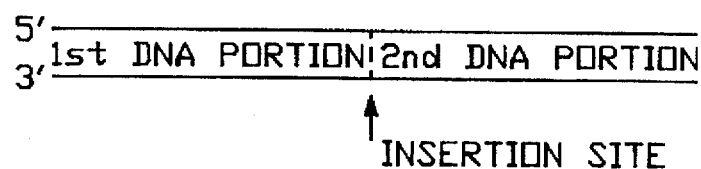
FIG._2B
EXCISION LINKER
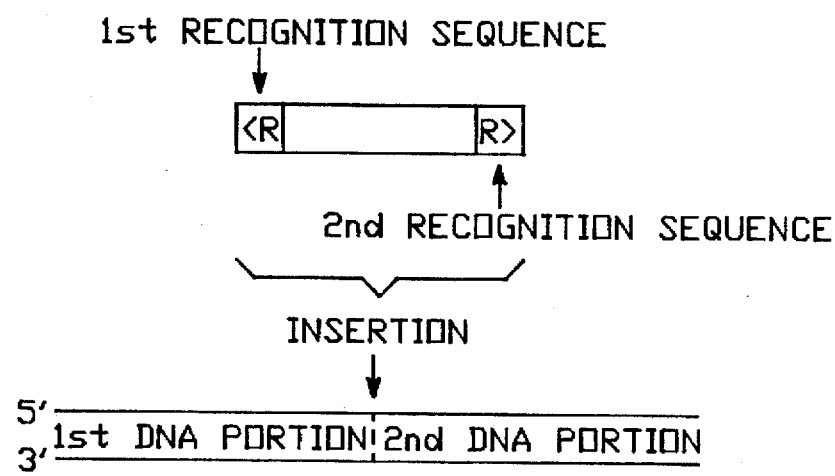
FIG._2C
FIRST MODIFIED DNA
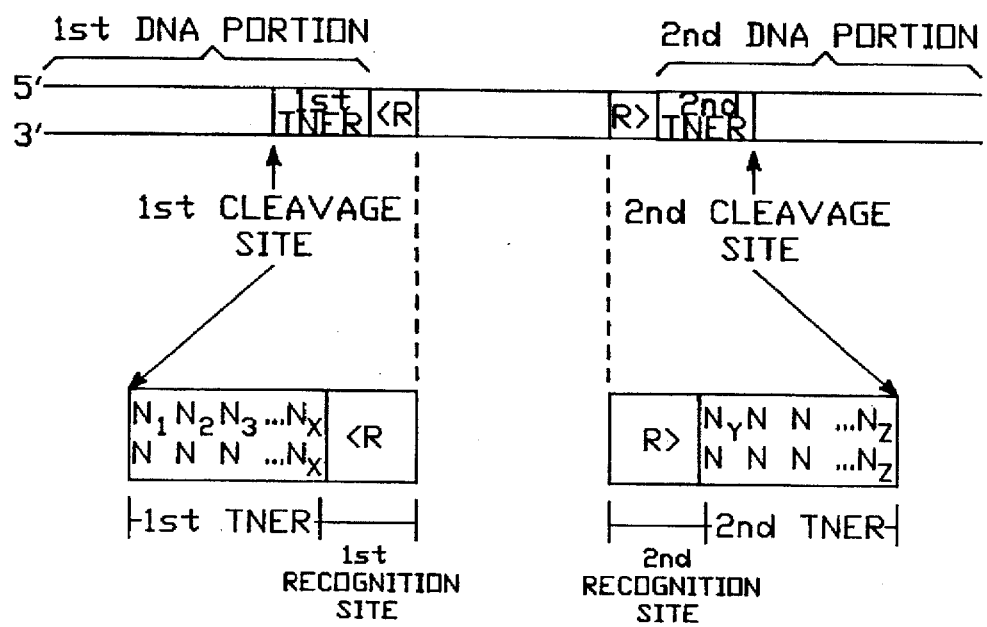

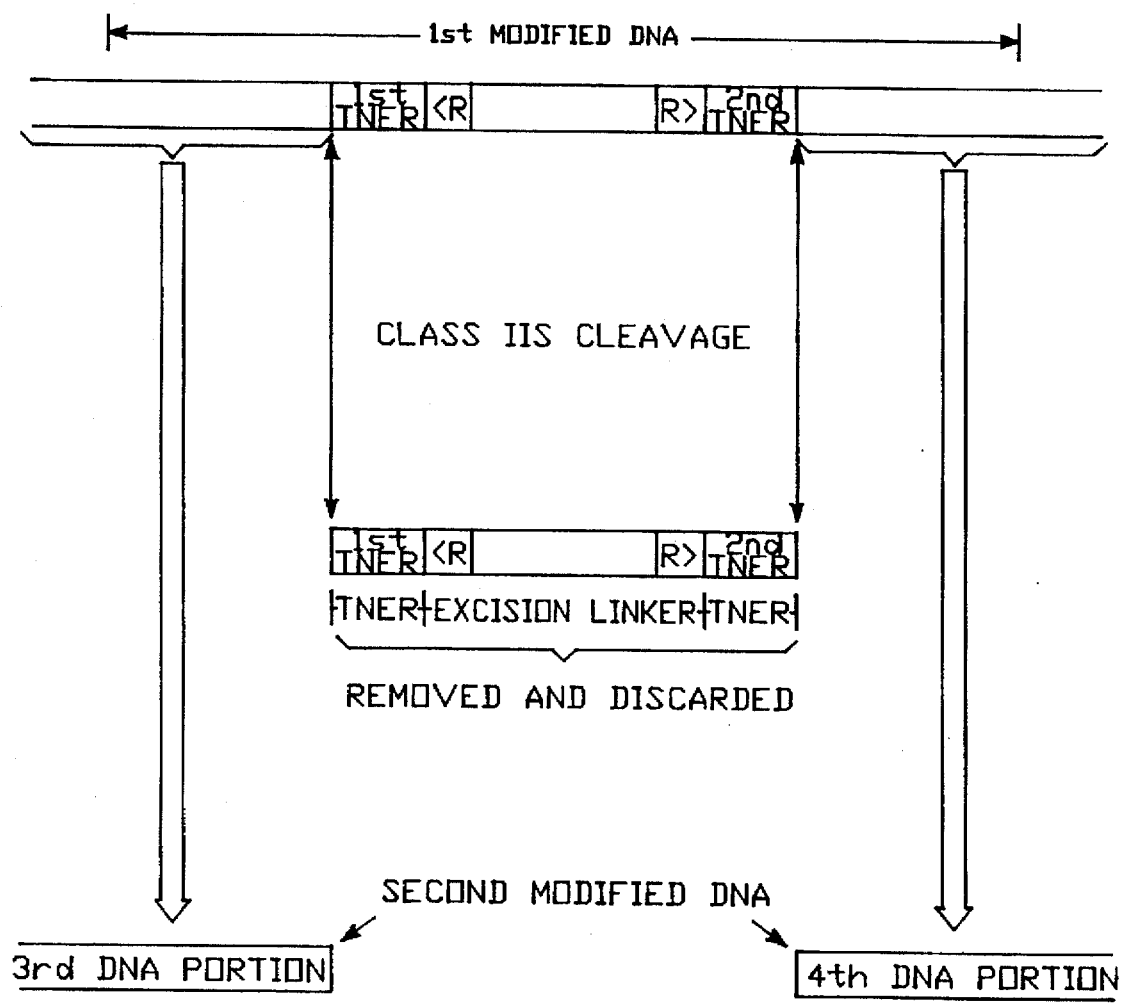
FIG._2D

FIG._2E
MUTATION LINKER
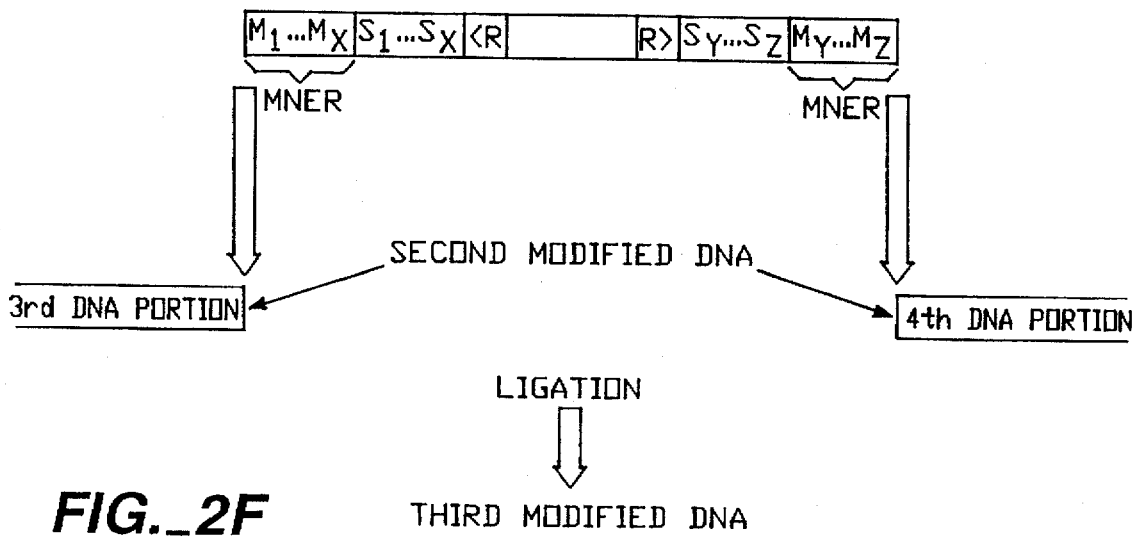
FIG._2F
THIRD MODIFIED DNA
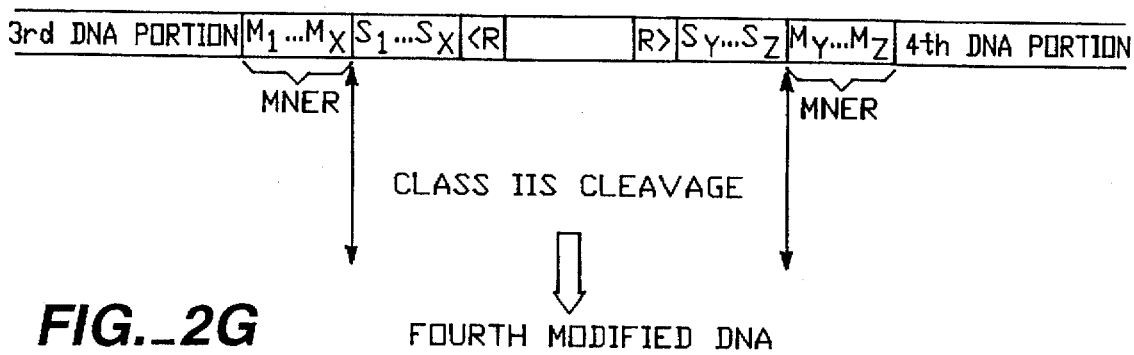
FIG._2G
FOURTH MODIFIED DNA
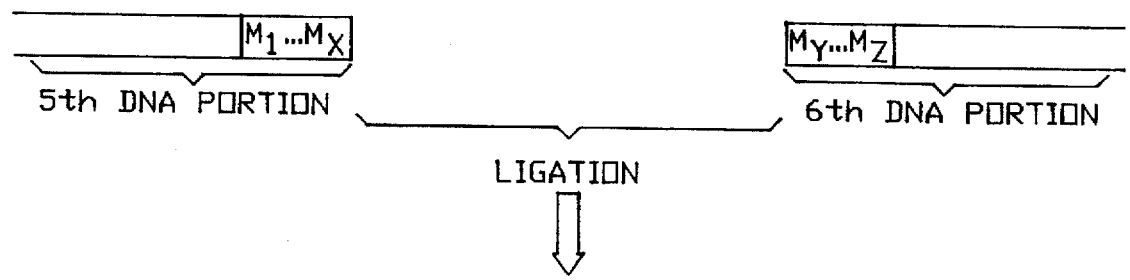
FIG._2H
MODIFIED TARGET DNA
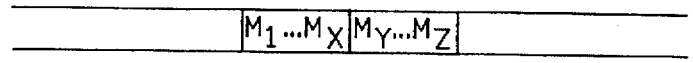

FIG._3
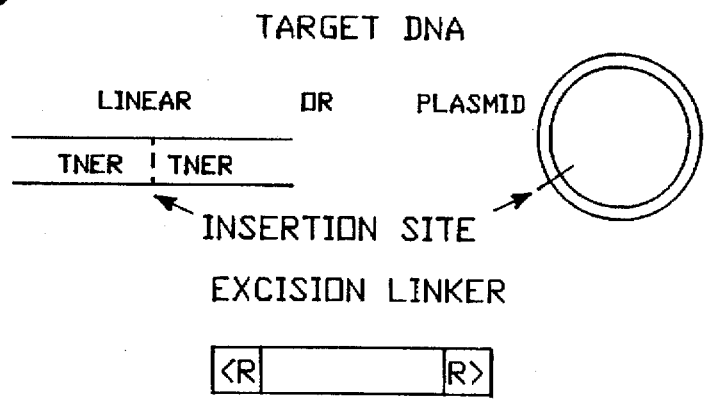
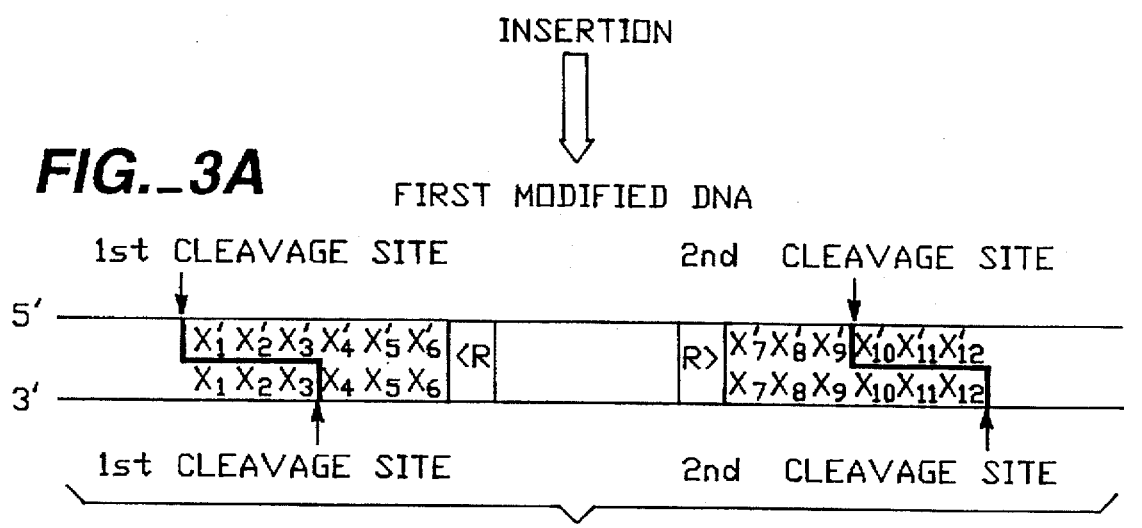
FIG._3A
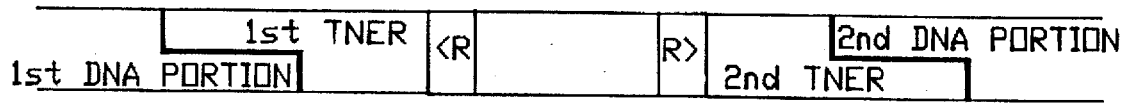
CLASS IIS CLEAVAGE
SECOND MODIFIED DNA
FIG._3B
1st DNA PORTION
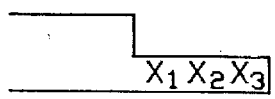
2nd DNA PORTION
END TAILORING

FIG._3C
END TAILORING
(C₁) EXONUCLEASE DIGESTION
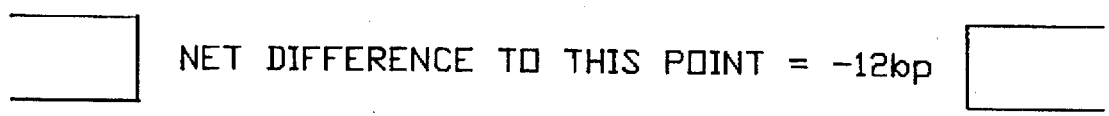
NET DIFFERENCE TO THIS POINT = −12bp
OR
(C₂) KLENOW POLYMERASE FILL-IN
NET DIFFERENCE = −6bp
TO THIS POINT
FIG._3D
MUTATION LINKER
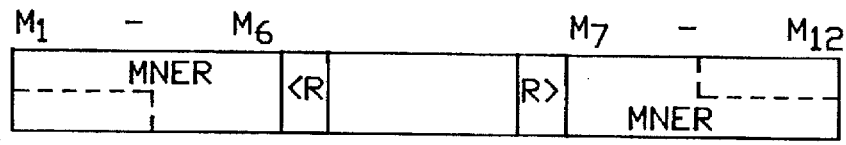
LIGATION
THIRD MODIFIED DNA
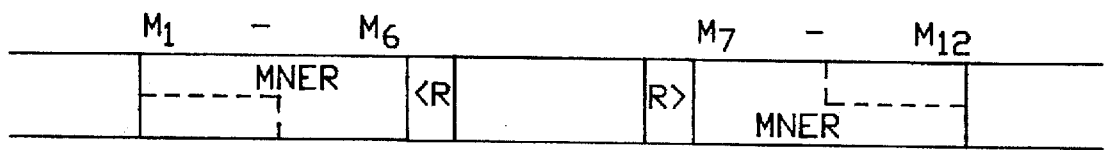
   CLASS IIS CLEAVAGE
AS IN (A) ABOVE   

FIG._3E  FOURTH MODIFIED DNA
FIG._3F
END TAILORING, KLENOW POLYMERASE FILL-IN.
FIG._3G
LIGATION
($G_1$) WHEN 2nd MODIFIED DNA WAS -12bp.
MODIFIED TARGET DNA
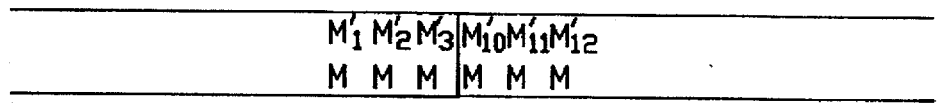
NET CHANGE = -6bp.
($G_1$) WHEN 2nd MODIFIED DNA WAS -6bp.
MODIFIED TARGET DNA
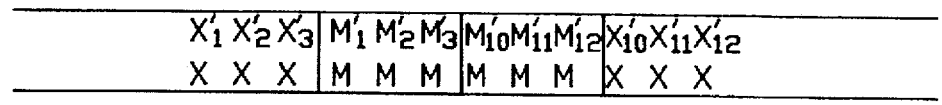
NET CHANGE = ONE-FOR-ONE SUBSTITUTION

FIG._4A

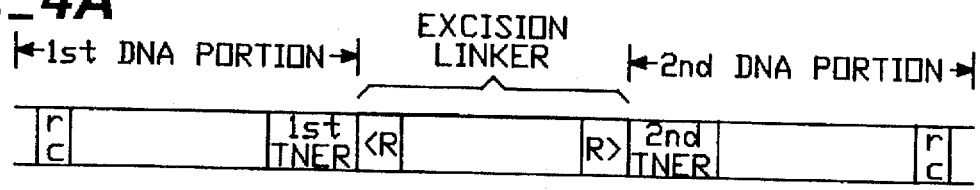

FIG._4B

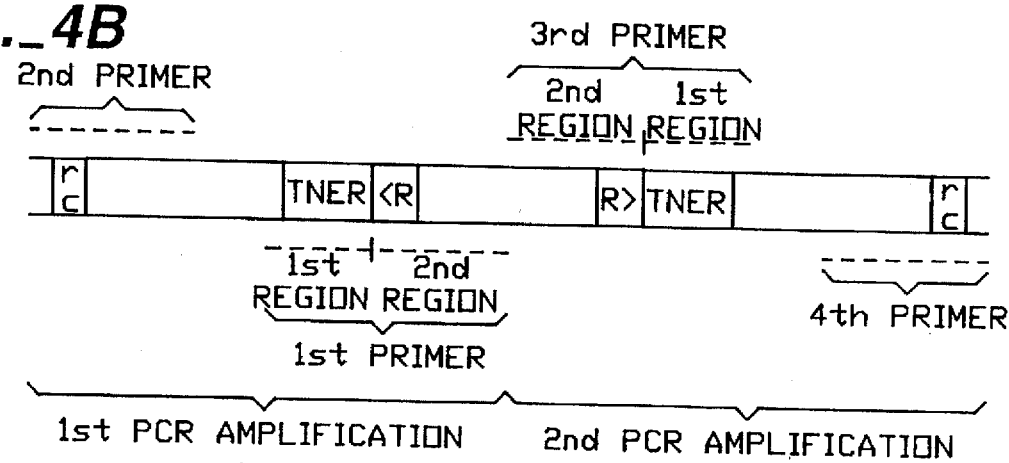

FIG._4C

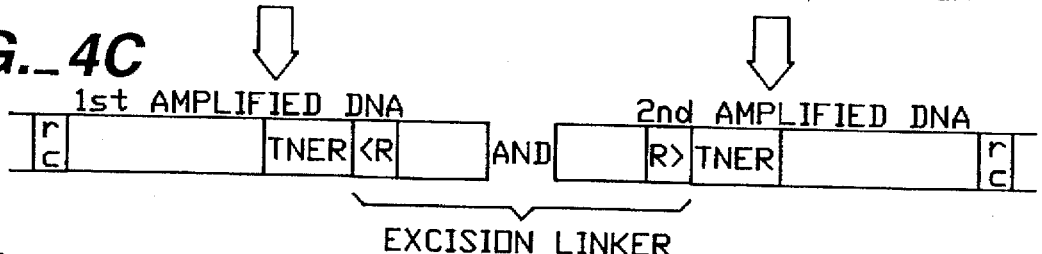

FIG._4D
DIGESTION OF TARGET DNA AND PRODUCTS OF (C) WITH ENZYMES COGNATE FOR [rc]

FIG._4E
THREE-WAY LIGATION WITH TARGET DNA YIELDS PRODUCT DEPICTED IN (A) ABOVE

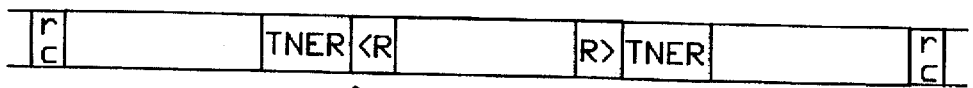

FIG._4

[rc] = RECOGNITION/CLEAVAGE SITE ENCODED IN TARGET DNA

TNER = TARGET NUCLEOTIDE END REGION

<R  
R>  } RECOGNITION SITE FOR A CLASS IIS RESTRICTION ENDONUCLEASE, ORIENTED SO THAT CLEAVAGE SITE LIES IN DIRECTION OF ARROWHEAD.

FIG._5A
INTENDED INSERTION SITE IN bla GENE → pBG66 PLASMID (EcoRI, NruI, 3', 5')

FIG._5B
TARGET DNA — PRIMER b, NdeI, INSERTION SITE, PRIMER a, BspMI, EcoRI
1st PCR PROCESS YIELDS

FIG._5C
1st HALF OF EXCISION LINKER — NdeI, INSERTION SITE, BspMI, EcoRI

FIG._5D
TARGET DNA — BspMI, PRIMER c, EcoRI, PRIMER d
2nd PCR PROCESS YIELDS, INSERTION SITE

FIG._5E
2nd HALF OF EXCISION LINKER — EcoRI, BspMI, EcoRI

FIG._5F
NdeI AND EcoRI DIGESTION OF (A), (C), AND (E)
FIG._5G
3-WAY LIGATION OF PRODUCTS OF (F)
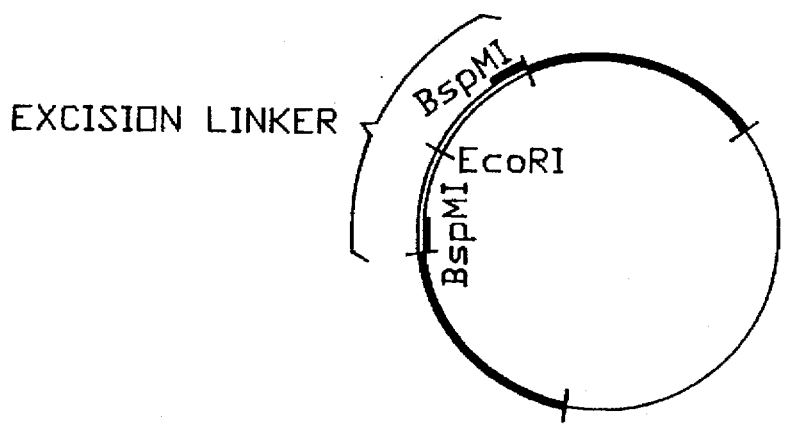
EXCISION LINKER
BspMI
BspMI
EcoRI
FIG._5
```
---------  =  PRIMER SEQUENCE HOMOLOGOUS
              TO TARGET DNA STRAND
  BspMI    =  RECOGNITION SITE FOR CLASS II
             RESTRICTION ENDONUCLEASE
```

FIG._6A
pBG66

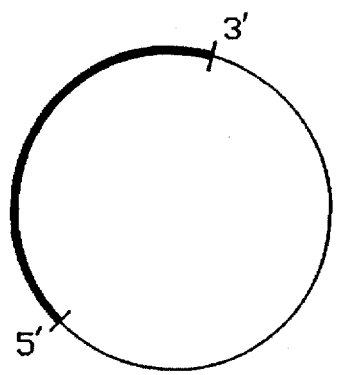

FIG._6B
EXCISION LINKER

```
         Eco RI       Bsp MI
GCAGGTCTGCAGGAATTCCTCGAGACCTGC
CGTCCAGACGTCCTTAAGGAGCTCTGGACG
Bsp MI
```

FIG._6C
INSERTION INTO bla TO FORM 1st MODIFIED DNA

```
       S   T   F   K   V   L
    5' AGC ACT TTT AAA GTT CTG 3'
    3' TCG TGA AAA TTT CAA GAC 5'
```

```
       S   T   F                            Eco RI       Bsp MI  K   V   L
    5' AGC ACT TTT GCAGGTCTGCAGGAATTCCTCGAGACCTGC AAA GTT CTG 3'
    3' TCG TGA AAA CGTCCAGACGTCCTTAAGGAGCTCTGGACG TTT CAA GAC 5'
                   Bsp MI
```

FIG._6D
BspMI DIGESTION TO FORM 2nd MODIFIED DNA

```
5' A                                          TT CTG 3'
3' TCG TG                                         C 5'
```

FIG._6E
KLENOW POLYMERASE FILL-IN

```
5' AGC AC                                     TT CTG 3'
3' TCG TG                                     AA GAC 5'
```

FIG._6F
MUTATION LINKER

```
                                          Bsp MI
NNNNGATCGCAGGTCGCGATTGTGAGCGGATAACAACCTGCAGTCNNNN
NNNNCTAGCGTCCAGCGCTAACACTCGCCTATTGTTGGACGTCAGNNNN
 Bsp MI                                   lacO
```

FIG._6G
LIGATION TO FORM 3rd MODIFIED DNA

```
                                               Bsp MI
5' AGC AC NNNNGATCGCAGGTCGCGATTGTGAGCGGATAACAACCTGCAGTCNNNN TT CTG 3'
3' TCG TG NNNNCTAGCGTCCAGCGCTAACACTCGCCTATTGTTGGACGTCAGNNNN AA GAC 5'
           Bsp MI                                   lacO
```

FIG._6H
BspMI DIGESTION TO FORM 4th MODIFIED DNA

```
5' AGC AC                                NNNN TT CTG 3'
3' TCG TG NNNN                                AA GAC 5'
```

FIG._6I
KLENOW FILL-IN

```
5' AGC AC NNNN                           NNNN TT CTG 3'
3' TCG TG NNNN                           NNNN AA GAC 5'
```

FIG._6J
RECIRCULARIZE PLASMID WITH LIGASE

```
            S   T
5' AGC ACN NNN NNN NTT CTG 3'
3' TCG TGN NNN NNN NAA GAC 5'
```

FIG._7

```
  M   S   I   Q   H   F   R   V   A   L   I   P   F   F   A   A   F   C
 ATG AGT ATT CAA CAT TTC CGT GTC GCC CTT ATT CCC TTT TTT GCG GCA TTT TGC

L   P   V   F   A   H   P   E   T   L   V   K   V   K   D   A   E   D
 CTT CCT GTT TTT GCT CAC CCA GAA ACG CTG GTG AAA GTA AAA GAT GCT GA|A GAT|
                                                                    ↑
  Q   L   G   A   R   V   G   Y   I   E   L   D   L   N   S   G   K   I
|CAG TTG GGT GC|A CGA GTG GGT TAC ATC GAA CTG GAT CTC AAC AGC GGT AAG ATC
   blaC14 ↑

L   E   S   F   R   P   E   E   R   F   P   M   M   S   T   F   K   V
 CTT GAG AGT TTT CGC CCC GAA GAA CGT TTT CCA ATG |ATG AGC AC|T |TTT AAA GT|T
                                                   blaC67↑           ↑blaC66

L   L   C   G   A   V   L   S   R   V   D   A   G   Q   E   Q   L   G
 CTG CTA TGT GGC GCG GTA TTA TCC CGT GTT GAC GCC GGG CAA GAG CAA CTC GGT

R   R   I   H   Y   S   Q   N   D   L   V   E   Y   S   P   V   T   E
 CGC CGC ATA CAC TAT TCT CAG AAT GAC TTC |GTT GAG TA|C TCA CCA GTC ACA GAA
                                              ↑blaC75

K   H   L   T   D   G   M   T   V   R   E   L   C   S   A   A   I   T
 AAG CAT CTT ACG GAT GGC ATG ACA GTA AGA GAA TTA TGC AGT GCT GCC ATA ACC

M   S   D   N   T   A   A   N   L   L   L   T   T   I   G   G   P   K
 ATG |AGT GAT AA|C ACT |GCG GCC AA|C TTA CTT CTG ACA ACG ATC GGA GGA CCG AAG
        ↑blaC76         ↑blaC80

E   L   T   A   F   L   H   N   M   G   D   H   V   T   R   L   D   R
 |GAG CTA A|CC GCT TTT TTG CAC AAC ATG GGG |GAT CAT GTA A|CT CGC CTT GAT CGT
     ↑BlaC86                                  ↑    ↑blaCI W   E   P   E   L   D   E   A   I   P   N   D   E   R   D   T   T   M
 TGC GAA CCG G|AG CTG AAT| GAA GCC ATA CCA AAC GAC GAG CGT GAC ACC ACG A|TG
               ↑blaC73

P   A   A   M   A   T   T   L   R   K   L   L   T   G   E   L   L   T
 |CCT GCA GCA A|TG GCA ACA ACG TTG CGC AAA CTA TTA ACT GG|C GAA CTA CTT ACT|
    ↑blaC7↑                                              ↑        ↑blaC31

L   A   S   R   Q   Q   L   I   D   W   M   E   A   D   K   V   A   G
 CTA GCT TCC CGG CAA CAA TTA A|TA GAC TGG| ATG GAG GCG GAT AAA GTT GCA GGA
                                ↑blaC83

P   L   L   R   S   A   L   P   A   G   W   F   I   A   D   K   S   G
 CCA CTT CTG CGC |TCG GCC CT|T CCG GCT GGC TGG TTT ATT GC|T GAT AAA T|CT GGA
                    ↑blaC82                               blaC70↑ blaC71↑

A   G   E   R   G   S   R   G   I   I   A   A   L   G   P   D   G   K
 |GCC GGT GAG C|GT GGG TCT CGC GGT ATC ATT GCA GCA CT|G GGA CCA G|AT GGT AAG
     ↑blaC74                                           ↑blaC81

P   S   R   I   V   V   I   Y   T   T   G   S   Q   A   T   M   D   E
 CCC TCC CG|T ATC GTA G|TT ATC TAC ACG ACG GGG AGT CAG GCA ACT ATG GAT GAA
            ↑blaC84

R   N   R   Q   I   A   E   I   G   A   S   L   I   K   H   W
 CGA AAT AGA CAG ATC GCT GAG ATA GGT GCC TCA CT|G ATT AAG C|AT TGG
                                                 ↑blaC85
```

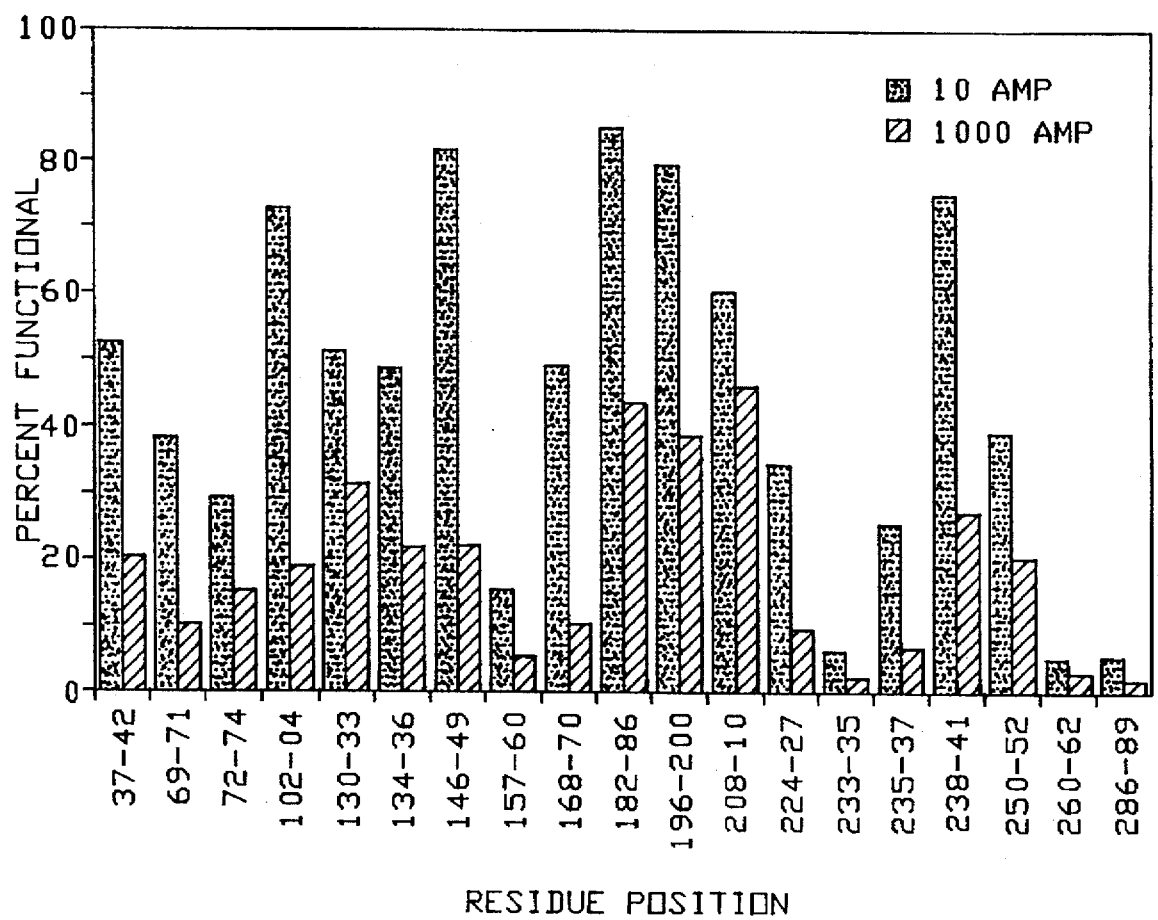
FIG._8

FIG._9

| aa RESIDUE: | | | 72 | 73 | 74 | 75 | 76 |
|---|---|---|---|---|---|---|---|
| RTEM β-LACTAMASE | | ser | thr | PHE | LYS | VAL | leu | leu |
| blaC66 1 mg/ml REPLACEMENTS | | | | | | | |
| MC-34,26 | | ser | thr | PHE | LYS | VAL | leu | leu |
| MC-2 | | ser | thr | PHE | LYS | LEU | leu | leu |
| CA-33 | | ser | thr | VAL | LYS | VAL | leu | leu |
| blaC66 10 µg/ml REPLACEMENTS | | | | | | | |
| MC-35,43 | | ser | thr | CYS | LYS | ILE | leu | leu |
| MC-6 | | ser | thr | SER | LYS | ILE | leu | leu |
| MC-27, CA-27 | | ser | thr | GLN | LYS | VAL | leu | leu |
| CA-1,24 | | ser | thr | LEU | LYS | ILE | leu | leu |
| CA-28 | | ser | thr | TYR | LYS | ILE | leu | leu |
| CA-30 | | ser | thr | THR | LYS | VAL | leu | leu |
| CA-31 | | ser | thr | LYS | LYS | VAL | leu | leu |
| CA-32 | | ser | thr | TRP | LYS | VAL | leu | leu |
| CA-34 | | ser | thr | VAL | LYS | ILE | leu | leu |
| CA-20 | | ser | thr | LEU | ARG | VAL | leu | leu |
| CA-29 | | ser | thr | VAL | ARG | ILE | leu | leu |
| CA-35 | | ser | thr | ALA | ASN | VAL | leu | leu |

FIG._10

| aa RESIDUE: | | 196 | 197 | 198 | 199 | 200 | | |
|---|---|---|---|---|---|---|---|---|
| RTEM β-LACTAMASE | | | | | | | | |
| | leu | thr | GLY | GLU | LEU | LEU | THR | leu | ala | blaC31 1 mg/ml REPLACEMENTS

| | | | | | | | | |
|---|---|---|---|---|---|---|---|---|
| MC-1 | leu | thr | ALA | ASP | LEU | ILE | SER | leu | ala |
| MC-2 | leu | thr | ALA | PRO | THR | PHE | THR | leu | ala |
| MC-3 | leu | thr | GLY | PRO | SER | VAL | ALA | leu | ala |
| MC-8 | leu | thr | ASP | ARG | GLN | ARG | ALA | leu | ala |
| MC-16 | leu | thr | ALA | SER | SER | VAL | THR | leu | ala | blaC31 10 μg/ml REPLACEMENTS

| | | | | | | | | |
|---|---|---|---|---|---|---|---|---|
| CA-1 | leu | thr | ALA | ARG | PRO | GLN | THR | leu | ala |
| CA-2 | leu | thr | VAL | TYR | HIS | ARG | GLU | leu | ala |
| CA-3 | leu | thr | ALA | PRO | GLY | THR | ALA | leu | ala |
| CA-4 | leu | thr | ALA | LEU | GLY | ARG | ASP | leu | ala |
| CA-5 | leu | thr | ALA | ARG | SER | SER | GLY | leu | ala |
| CA-6 | leu | thr | GLY | PHE | ARG | ARG | LYS | leu | ala |

FIG._11

| aa RESIDUE: | 37 | 38 | 39 | 40 | 41 | 42 | | |
|---|---|---|---|---|---|---|---|---|
| RTEM β-LACTAMASE | | | | | | | | |
| | asp | ala | GLU | ASP | GLN | LEU | GLY | ALA | arg | val |
| blaC14 1 mg/ml REPLACEMENTS | | | | | | | | |
| MC-26 | asp | ala | ALA | ALA | LEU | LEU | LYS | ALA | arg | val |
| MC-27 | asp | ala | ALA | SER | ALA | LEU | ALA | ALA | arg | val |
| MC-29 | asp | ala | GLU | --- | LEU | GLY | ASN | GLN | arg | val |
| MC-31 | asp | ala | GLU | ARG | TYR | THR | GLN | SER | arg | val |
| blaC14 10 μg/ml REPLACEMENTS | | | | | | | | |
| CA-3 | asp | ala | ASP | SER | PHE | GLU | GLU | THR | arg | val |
| CA-1 | asp | ala | ALA | SER | LEU | MET | ARG | GLY | arg | val |
| CA-9 | asp | ala | ALA | GLY | GLY | ARG | PHE | GLY | arg | val |
| CA-8 | asp | ala | ALA | --- | ILE | CYS | GLY | GLY | arg | val |
| CM-2 | asp | ala | GLU | VAL | PHE | THR | ASN | GLU | arg | val |
| CM-5 | asp | ala | ASP | ARG | ASN | GLY | GLN | LEU | arg | val |
| CA-4 | asp | ala | ASP | VAL | GLN | ASN | GLU | THR | arg | val |
| CA-5 | asp | ala | ASP | CYS | ILE | ALA | SER | GLY | arg | val |
| CA-6 | asp | ala | ALA | VAL | VAL | LYS | GLY | GLN | arg | val |
| CA-2 | asp | ala | ALA | SER | PHE | LYS | GLY | GLU | arg | val |
| CM-1 | asp | ala | ALA | PHE | CYS | HIS | PRO | GLY | arg | val |
| CM-4 | asp | ala | VAL | LEU | SER | GLY | LEU | THR | arg | val |
| BblaC14 NON-FUNCTIONAL REPLACEMENTS | | | | | | | | |
| CP-1 | asp | ala | ALA | LEU | PRO | THR | ASP | LYS | arg | val |
| CP-14 | asp | ala | VAL | TRP | SER | ILE | ASP | ARG | arg | val |
| CP-15 | asp | ala | VAL | SER | SER | GLU | ARG | LYS | arg | val |
| CP-16 | asp | ala | VAL | PHE | GLU | GLY | ASN | ARG | arg | val |
| CP-17 | asp | ala | ALA | SER | LEU | ARG | GLY | LYS | arg | val |
| CP-20 | asp | ala | ALA | VAL | VAL | ARG | LEU | LYS | arg | val |
| CP-21 | asp | ala | ALA | LEU | ARG | THR | HIS | LYS | arg | val |

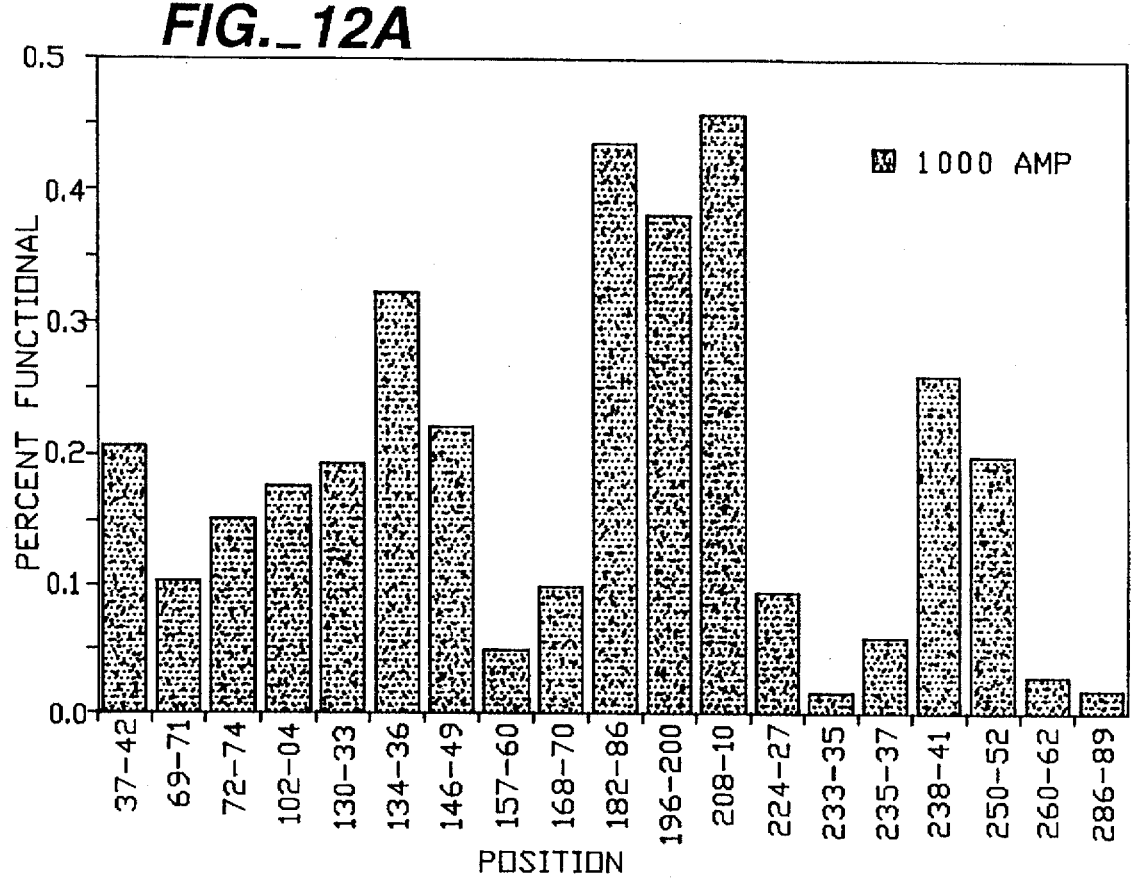
FIG._12A
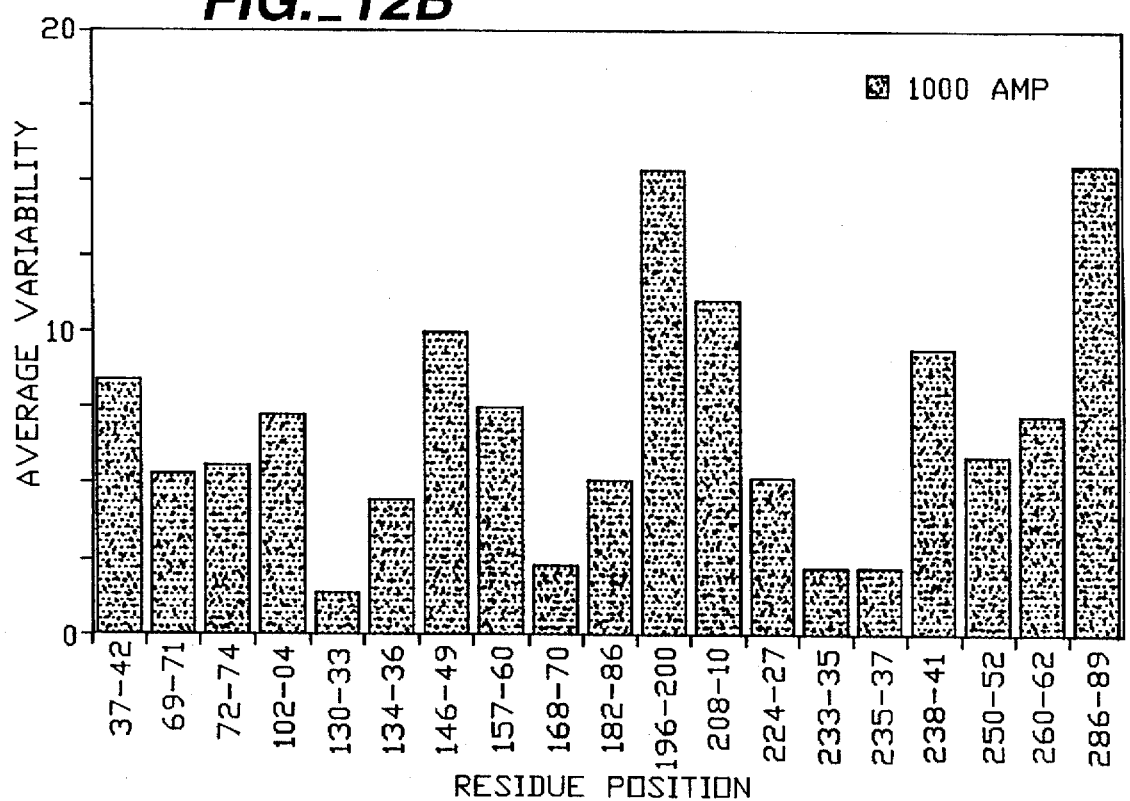
FIG._12B

FIG._13

```
 M   S   I   Q   H   F   R   V   A   L   I   P   F   F   A   A   F   C
ATG AGT ATT CAA CAT TTC CGT GTC GCC CTT ATT CCC TTT TTT GCG GCA TTT TGC

L   P   V   F   A   H   P   E   T   L   V   K   V   K   D   A   E   D
CTT CCT GTT TTT GCT CAC CCA GAA ACG CTG GTG AAA GTA AAA GAT GCT GAA GAT

Q   L   G   A   R   V   G   Y   I   E   L   D   N   S   G   K   I
CAG TTG GGT GCA CGA GTG GGT TAC ATC GAA CTG GAT CTC AAC AGC GGT AAG ATC

L   E   S   F   R   P   E   E   R   F   P   M   M   S   T   F   K   V
CTT GAG AGT TTT CGC CCC GAA GAA CGT TTT CCA AGT [ATG AGC ACT TTT AAA G]TT
                                                blaC67              blaC66

L   L   C   G   A   V   L   S   R   V   D   A   G   Q   E   Q   L   G
CTG CTA TGT GGC GCG GTA TTA TCC CGT GTT GAC GCC GGG CAA GAG CAA CTC GGT

R   R   I   H   Y   S   Q   N   D   L   V   E   Y   S   P   V   T   E
CGC CGC ATA CAC TAT TCT CAG AAT GAC TTC [GTT GAG TAC] TCA CCA GTC ACA GAA
                                         blaC75

K   H   L   T   D   G   M   T   V   R   E   L   C   S   A   A   I   T
AAG CAT CTT ACG GAT GGC ATG ACA GTA AGA GAA TTA TGC AGT GCT GCC ATA ACC

M   S   D   N   T   A   A   N   L   L   L   T   T   I   G   G   P   K
ATG [AGT GAT AAC] ACT GCG GCC AAC TTA CTT CTG ACA ACG ATC GGA GGA CCG AAG
     blaC76

E   L   T   A   F   L   H   N   M   G   D   H   V   T   R   L   D   R
GAG CTA ACC GCT TTT TTG CAC AAC ATG GGG GAT CAT GTA ACT CGC CTT GAT CGT

W   E   P   E   L   D   E   A   I   P   N   D   E   R   D   T   T   M
TGC [GAA CCG GAG CTG AAT] GAA GCC ATA CCA AAC GAC GAG CGT GAC ACC ACG ATG
     blaC72      ↑blaC73

P   A   A   M   A   T   T   L   R   K   L   L   T   G   E   L   L   T
CCT GCA GCA ATG GCA ACA ACG TTG CGC AAA CTA TTA ACT GGC GAA CTA CTT ACT

L   A   S   R   Q   Q   L   I   D   W   M   E   A   D   K   V   A   G
CTA GCT TCC CGG CAA CAA TTA ATA GAC TGG ATG GAG GCG GAT AAA GTT GCA GGA

P   L   L   R   S   A   L   P   A   G   W   F   I   A   D   K   S   G
CCA CTT CTG CGC TCG GCC CTT CCG GCT GGC TGG TTT ATT GC[T GAT AAA T]CT GGA
                                                        blaC70   blaC71

A   G   E   R   G   S   R   G   I   I   A   A   L   G   P   D   G   K
[GCC GGT GAG C]GT GGG TCT CGC GGT ATC ATT GCA GCA CTG GGG CCA GAT GGT AAG
 blaC74

P   S   R   I   V   V   I   Y   T   T   G   S   Q   A   T   M   D   E
CCC TCC CGT ATC GTA GTT ATC TAC ACG ACG GGG AGT CAG GCA ACT ATG GAT GAA

R   N   R   Q   I   A   E   I   G   A   S   L   I   K   H   W
CGA AAT AGA CAG ATC GCT GAG ATA GGT GCC TCA CTG ATT AAG CAT TGG
```

FIG._14
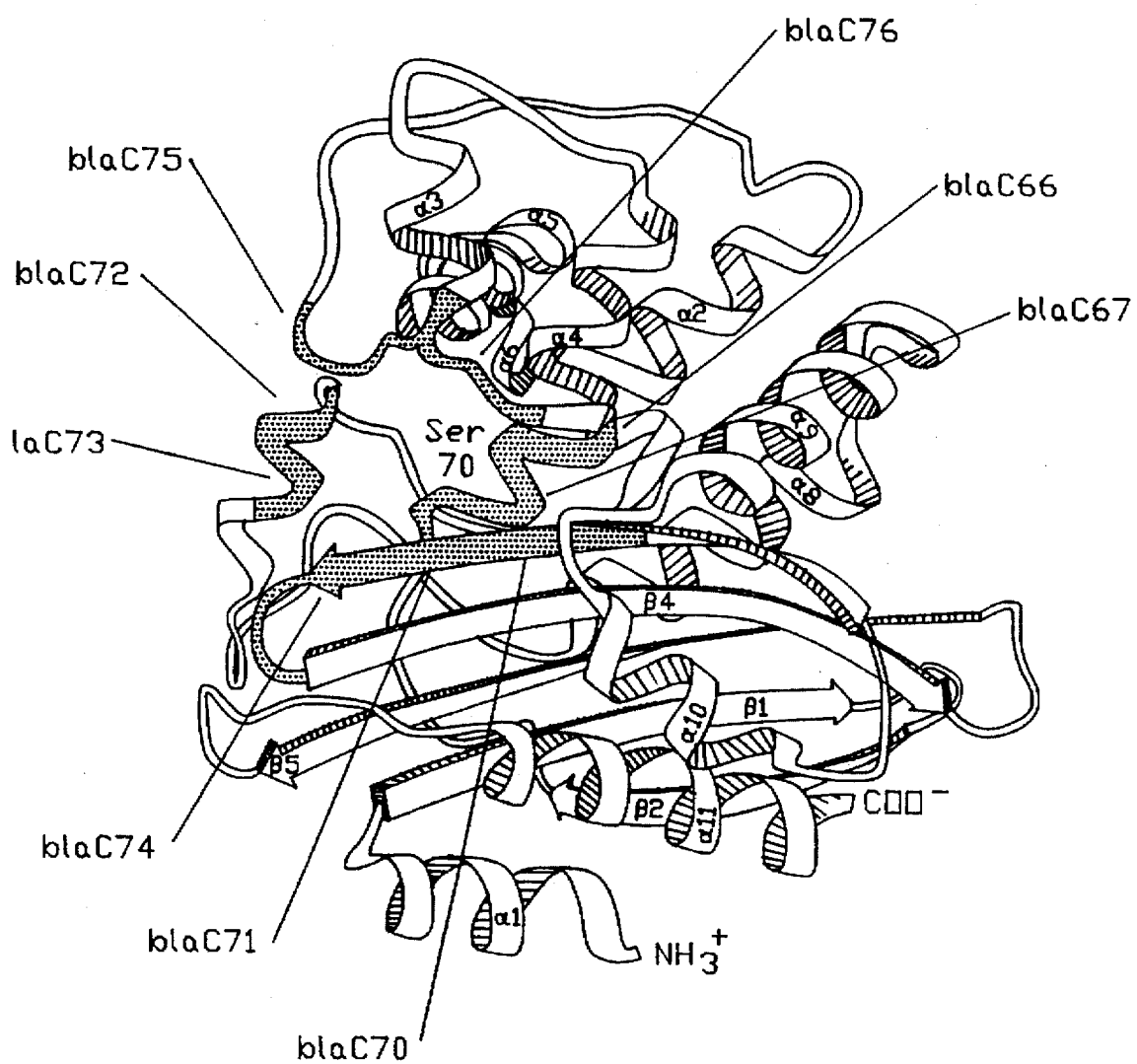

FIG._15

RTEM β-LACTAMASE

| | | | | | | | |
|---|---|---|---|---|---|---|---|
| wt | asp | lys | SER | GLY | ALA | gly | glu |

10 μg/ml AMP: 100 μg/ml CEPHALOSPORIN C

| | | | | | | | |
|---|---|---|---|---|---|---|---|
| CC-6 | asp | lys | SER | GLY | ASN | gly | glu |
| CC-20 | asp | lys | SER | GLY | SER | gly | glu |

FIG._16

RTEM β-LACTAMASE

| wt | | gly | ala | GLY | GLU | ARG | gly | ser |
|---|---|---|---|---|---|---|---|---|

1 mg/ml AMP REPLACEMENTS

| 3-27 | gly | ala | GLY | TYR | ASP | gly | ser |
|---|---|---|---|---|---|---|---|
| 3-25 | gly | ala | GLY | ARG | HIS | gly | ser |
| 1-10 | gly | ala | GLY | GLN | PRO | gly | ser |
| 5-21 | gly | ala | –   | CYS | PRO | gly | ser |

1 mg/ml AMP: .05 µg/ml CEFOTAXIME RESISTANT REPLACEMENTS

| 1-34 | gly | ala | SER | LYS | ASP | gly | ser |
|---|---|---|---|---|---|---|---|
| 1-24 | gly | ala | CYS | ASP | SER | gly | ser |

10 µg/ml AMP: .05 µg/ml CEFOTAXIME REPLACEMENTS

| 3-30 | gly | ala | SER | LYS | ARG | gly | ser |
|---|---|---|---|---|---|---|---|
| 3-4  | gly | ala | SER | SER | PRO | gly | ser |
| 4-15 | gly | ala | CYS | TYR | ASN | gly | ser |
| 3-20 | gly | ala | CYS | ASN | SER | gly | ser |
| 2-21 | gly | ala | SER | GLU | ASN | gly | ser |

10 µg/ml AMP REPLACEMENTS

| 1-1 | gly | ala | LEU | GLU | TYR | gly | ser |
|---|---|---|---|---|---|---|---|
| 1-2 | gly | ala | LEU | ARG | HIS | gly | ser |
| 1-6 | gly | ala | VAL | GLN | PRO | gly | ser |

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: double
( D ) TOPOLOGY: both ( i i ) MOLECULE TYPE: cDNA ( x i ) SEQUENCE DESCRIPTION: SEQ ID NO:1:

NNNNNNNGAG GCCTCNNNNN NN 22

( 2 ) INFORMATION FOR SEQ ID NO:2:

( i ) SEQUENCE CHARACTERISTICS:
( A ) LENGTH: 28 base pairs
( B ) TYPE: nucleic acid
( C ) STRANDEDNESS: double
( D ) TOPOLOGY: both ( i i ) MOLECULE TYPE: cDNA ( x i ) SEQUENCE DESCRIPTION: SEQ ID NO:2:

NNNNNNNNGC AGGTACCTGC NNNNNNNN 28

( 2 ) INFORMATION FOR SEQ ID NO:3:

( i ) SEQUENCE CHARACTERISTICS:
( A ) LENGTH: 30 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

GCAGGTCTGC AGGAATTCCT CGAGACCTGC 30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
GCAGGTCTCG AGGAATTCCT GCAGACCTGC                                    30
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:5:

```
AGCACTTTTA AAGTTCTG                                                 18
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:6:

```
CAGAACTTTA AAAGTGCT                                                 18
```

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:7:

```
AGCACTTTTG CAGGTCTGCA GGAATTCCTC GAGACCTGCA AAGTTCTG                48
```

( 2 ) INFORMATION FOR SEQ ID NO:8:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:8:

```
CAGAACTTTG CAGGTCTCGA GGAATTCCTG CAGACCTGCA AAAGTGCT                48
```

( 2 ) INFORMATION FOR SEQ ID NO:9:

( i ) SEQUENCE CHARACTERISTICS:

(A) LENGTH: 49 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:9:

NNNNGATCGC AGGTCGCGAT TGTGAGCGGA TAACAACCTG CAGTCNNNN 49

(2) INFORMATION FOR SEQ ID NO:10:

(i) SEQUENCE CHARACTERISTICS:
(A) LENGTH: 49 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:10:

NNNNGACTGC AGGTTGTTAT CCGCTCACAA TCGCGACCTG CGATCNNNN 49

(2) INFORMATION FOR SEQ ID NO:11:

(i) SEQUENCE CHARACTERISTICS:
(A) LENGTH: 59 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:11:

AGCACNNNNG ATCGCAGGTC GCGATTGTGA GCGGATAACA ACCTGCAGTC NNNNTTCTG 59

(2) INFORMATION FOR SEQ ID NO:12:

(i) SEQUENCE CHARACTERISTICS:
(A) LENGTH: 59 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:12:

CAGAANNNNG ACTGCAGGTT GTTATCCGCT CACAATCGCG ACCTGCGATC NNNNGTGCT 59

(2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:13:

AGCACNNNNN NNNTTCTG 18

(2) INFORMATION FOR SEQ ID NO:14:

(i) SEQUENCE CHARACTERISTICS:
(A) LENGTH: 18 base pairs
(B) TYPE: nucleic acid
(C) STRANDEDNESS: double
(D) TOPOLOGY: circular ( i i ) MOLECULE TYPE: cDNA ( x i ) SEQUENCE DESCRIPTION: SEQ ID NO:14:

CAGAANNNNN NNNGTGCT                                                                                    18

( 2 ) INFORMATION FOR SEQ ID NO:15:

( i ) SEQUENCE CHARACTERISTICS:
        ( A ) LENGTH: 858 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..858

( x i ) SEQUENCE DESCRIPTION: SEQ ID NO:15:

```
ATG  AGT  ATT  CAA  CAT  TTC  CGT  GTC  GCC  CTT  ATT  CCC  TTT  TTT  GCG  GCA      48
Met  Ser  Ile  Gln  His  Phe  Arg  Val  Ala  Leu  Ile  Pro  Phe  Phe  Ala  Ala
 1              5                        10                       15

TTT  TGC  CTT  CCT  GTT  TTT  GCT  CAC  CCA  GAA  ACG  CTG  GTG  AAA  GTA  AAA      96
Phe  Cys  Leu  Pro  Val  Phe  Ala  His  Pro  Glu  Thr  Leu  Val  Lys  Val  Lys
               20                       25                       30

GAT  GCT  GAA  GAT  CAG  TTG  GGT  GCA  CGA  GTG  GGT  TAC  ATC  GAA  CTG  GAT     144
Asp  Ala  Glu  Asp  Gln  Leu  Gly  Ala  Arg  Val  Gly  Tyr  Ile  Glu  Leu  Asp
          35                        40                       45

CTC  AAC  AGC  GGT  AAG  ATC  CTT  GAG  AGT  TTT  CGC  CCC  GAA  GAA  CGT  TTT     192
Leu  Asn  Ser  Gly  Lys  Ile  Leu  Glu  Ser  Phe  Arg  Pro  Glu  Glu  Arg  Phe
     50                       55                       60

CCA  ATG  ATG  AGC  ACT  TTT  AAA  GTT  CTG  CTA  TGT  GGC  GCG  GTA  TTA  TCC     240
Pro  Met  Met  Ser  Thr  Phe  Lys  Val  Leu  Leu  Cys  Gly  Ala  Val  Leu  Ser
65                       70                       75                      80

CGT  GTT  GAC  GCC  GGG  CAA  GAG  CAA  CTC  GGT  CGC  CGC  ATA  CAC  TAT  TCT     288
Arg  Val  Asp  Ala  Gly  Gln  Glu  Gln  Leu  Gly  Arg  Arg  Ile  His  Tyr  Ser
                    85                       90                       95

CAG  AAT  GAC  TTC  GTT  GAG  TAC  TCA  CCA  GTC  ACA  GAA  AAG  CAT  CTT  ACG     336
Gln  Asn  Asp  Phe  Val  Glu  Tyr  Ser  Pro  Val  Thr  Glu  Lys  His  Leu  Thr
               100                      105                     110

GAT  GGC  ATG  ACA  GTA  AGA  GAA  TTA  TGC  AGT  GCT  GCC  ATA  ACC  ATG  AGT     384
Asp  Gly  Met  Thr  Val  Arg  Glu  Leu  Cys  Ser  Ala  Ala  Ile  Thr  Met  Ser
          115                      120                     125

GAT  AAC  ACT  GCG  GCC  AAC  TTA  CTT  CTG  ACA  ACG  ATC  GGA  GGA  CCG  AAG     432
Asp  Asn  Thr  Ala  Ala  Asn  Leu  Leu  Leu  Thr  Thr  Ile  Gly  Gly  Pro  Lys
     130                      135                      140

GAG  CTA  ACC  GCT  TTT  TTG  CAC  AAC  ATG  GGG  GAT  CAT  GTA  ACT  CGC  CTT     480
Glu  Leu  Thr  Ala  Phe  Leu  His  Asn  Met  Gly  Asp  His  Val  Thr  Arg  Leu
145                      150                      155                     160

GAT  CGT  TGC  GAA  CCG  GAG  CTG  AAT  GAA  GCC  ATA  CCA  AAC  GAC  GAG  CGT     528
Asp  Arg  Cys  Glu  Pro  Glu  Leu  Asn  Glu  Ala  Ile  Pro  Asn  Asp  Glu  Arg
                    165                      170                     175

GAC  ACC  ACG  ATG  CCT  GCA  GCA  ATG  GCA  ACA  ACG  TTG  CGC  AAA  CTA  TTA     576
Asp  Thr  Thr  Met  Pro  Ala  Ala  Met  Ala  Thr  Thr  Leu  Arg  Lys  Leu  Leu
               180                      185                     190

ACT  GGC  GAA  CTA  CTT  ACT  CTA  GCT  TCC  CGG  CAA  CAA  TTA  ATA  GAC  TGG     624
Thr  Gly  Glu  Leu  Leu  Thr  Leu  Ala  Ser  Arg  Gln  Gln  Leu  Ile  Asp  Trp
          195                      200                     205

ATG  GAG  GCG  GAT  AAA  GTT  GCA  GGA  CCA  CTT  CTG  CGC  TCG  GCC  CTT  CCG     672
Met  Glu  Ala  Asp  Lys  Val  Ala  Gly  Pro  Leu  Leu  Arg  Ser  Ala  Leu  Pro
     210                      215                      220

GCT  GGC  TGG  TTT  ATT  GCT  GAT  AAA  TCT  GGA  GCC  GGT  GAG  CGT  GGG  TCT     720
```

| | | | | | | | | | | | | | | | |
|---|---|---|---|---|---|---|---|---|---|---|---|---|---|---|---|
| Ala | Gly | Trp | Phe | Ile | Ala | Asp | Lys | Ser | Gly | Ala | Gly | Glu | Arg | Gly | Ser |
| 225 | | | | 230 | | | | | 235 | | | | | | 240 |

| CGC | GGT | ATC | ATT | GCA | GCA | CTG | GGG | CCA | GAT | GGT | AAG | CCC | TCC | CGT | ATC | 768 |
|---|---|---|---|---|---|---|---|---|---|---|---|---|---|---|---|---|
| Arg | Gly | Ile | Ile | Ala | Ala | Leu | Gly | Pro | Asp | Gly | Lys | Pro | Ser | Arg | Ile | |
| | | | | 245 | | | | | 250 | | | | | 255 | | |

| GTA | GTT | ATC | TAC | ACG | ACG | GGG | AGT | CAG | GCA | ACT | ATG | GAT | GAA | CGA | AAT | 816 |
|---|---|---|---|---|---|---|---|---|---|---|---|---|---|---|---|---|
| Val | Val | Ile | Tyr | Thr | Thr | Gly | Ser | Gln | Ala | Thr | Met | Asp | Glu | Arg | Asn | |
| | | | 260 | | | | | 265 | | | | | 270 | | | |

| AGA | CAG | ATC | GCT | GAG | ATA | GGT | GCC | TCA | CTG | ATT | AAG | CAT | TGG | | | 858 |
|---|---|---|---|---|---|---|---|---|---|---|---|---|---|---|---|---|
| Arg | Gln | Ile | Ala | Glu | Ile | Gly | Ala | Ser | Leu | Ile | Lys | His | Trp | | | |
| | | 275 | | | | | 280 | | | | | 285 | | | | |

( 2 ) INFORMATION FOR SEQ ID NO:16:

( i ) SEQUENCE CHARACTERISTICS:
    ( A ) LENGTH: 286 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

| Met | Ser | Ile | Gln | His | Phe | Arg | Val | Ala | Leu | Ile | Pro | Phe | Phe | Ala | Ala |
|---|---|---|---|---|---|---|---|---|---|---|---|---|---|---|---|
| 1 | | | | 5 | | | | | 10 | | | | | 15 | |
| Phe | Cys | Leu | Pro | Val | Phe | Ala | His | Pro | Glu | Thr | Leu | Val | Lys | Val | Lys |
| | | | 20 | | | | | 25 | | | | | 30 | | |
| Asp | Ala | Glu | Asp | Gln | Leu | Gly | Ala | Arg | Val | Gly | Tyr | Ile | Glu | Leu | Asp |
| | | | 35 | | | | | 40 | | | | | 45 | | |
| Leu | Asn | Ser | Gly | Lys | Ile | Leu | Glu | Ser | Phe | Arg | Pro | Glu | Glu | Arg | Phe |
| | | | 50 | | | | | 55 | | | | | 60 | | |
| Pro | Met | Met | Ser | Thr | Phe | Lys | Val | Leu | Leu | Cys | Gly | Ala | Val | Leu | Ser |
| 65 | | | | | 70 | | | | | 75 | | | | | 80 |
| Arg | Val | Asp | Ala | Gly | Gln | Glu | Gln | Leu | Gly | Arg | Arg | Ile | His | Tyr | Ser |
| | | | | 85 | | | | | 90 | | | | | 95 | |
| Gln | Asn | Asp | Phe | Val | Glu | Tyr | Ser | Pro | Val | Thr | Glu | Lys | His | Leu | Thr |
| | | | | 100 | | | | | 105 | | | | | 110 | |
| Asp | Gly | Met | Thr | Val | Arg | Glu | Leu | Cys | Ser | Ala | Ala | Ile | Thr | Met | Ser |
| | | | 115 | | | | | 120 | | | | | 125 | | |
| Asp | Asn | Thr | Ala | Ala | Asn | Leu | Leu | Leu | Thr | Thr | Ile | Gly | Gly | Pro | Lys |
| | | 130 | | | | | 135 | | | | | 140 | | | |
| Glu | Leu | Thr | Ala | Phe | Leu | His | Asn | Met | Gly | Asp | His | Val | Thr | Arg | Leu |
| 145 | | | | | 150 | | | | | 155 | | | | | 160 |
| Asp | Arg | Cys | Glu | Pro | Glu | Leu | Asn | Glu | Ala | Ile | Pro | Asn | Asp | Glu | Arg |
| | | | | 165 | | | | | 170 | | | | | 175 | |
| Asp | Thr | Thr | Met | Pro | Ala | Ala | Met | Ala | Thr | Thr | Leu | Arg | Lys | Leu | Leu |
| | | | 180 | | | | | 185 | | | | | 190 | | |
| Thr | Gly | Glu | Leu | Leu | Thr | Leu | Ala | Ser | Arg | Gln | Gln | Leu | Ile | Asp | Trp |
| | | 195 | | | | | 200 | | | | | 205 | | | |
| Met | Glu | Ala | Asp | Lys | Val | Ala | Gly | Pro | Leu | Leu | Arg | Ser | Ala | Leu | Pro |
| 210 | | | | | 215 | | | | | 220 | | | | | |
| Ala | Gly | Trp | Phe | Ile | Ala | Asp | Lys | Ser | Gly | Ala | Gly | Glu | Arg | Gly | Ser |
| 225 | | | | | 230 | | | | | 235 | | | | | 240 |
| Arg | Gly | Ile | Ile | Ala | Ala | Leu | Gly | Pro | Asp | Gly | Lys | Pro | Ser | Arg | Ile |
| | | | | 245 | | | | | 250 | | | | | 255 | |
| Val | Val | Ile | Tyr | Thr | Thr | Gly | Ser | Gln | Ala | Thr | Met | Asp | Glu | Arg | Asn |
| | | | 260 | | | | | 265 | | | | | 270 | | |
| Arg | Gln | Ile | Ala | Glu | Ile | Gly | Ala | Ser | Leu | Ile | Lys | His | Trp | | |
| | | 275 | | | | | 280 | | | | | 285 | | | |

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Ser  Thr  Phe  Lys  Val  Leu  Leu
    1                       5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Ser  Thr  Phe  Lys  Val  Leu  Leu
    1                       5

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Ser  Thr  Phe  Lys  Leu  Leu  Leu
    1                       5

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Ser  Thr  Val  Lys  Val  Leu  Leu
    1                       5

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Ser  Thr  Cys  Lys  Ile  Leu  Leu
    1                       5

( 2 ) INFORMATION FOR SEQ ID NO:22:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Ser  Thr  Ser  Lys  Ile  Leu  Leu
1                    5
```

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Ser  Thr  Gln  Lys  Val  Leu  Leu
1                    5
```

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Ser  Thr  Leu  Lys  Ile  Leu  Leu
1                    5
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Ser  Thr  Tyr  Lys  Ile  Leu  Leu
1                    5
```

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Ser  Thr  Thr  Lys  Val  Leu  Leu
1                    5
```

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Ser Thr Lys Lys Val Leu Leu
1                5
```

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Ser Thr Trp Lys Val Leu Leu
1                5
```

( 2 ) INFORMATION FOR SEQ ID NO:29:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Ser Thr Val Lys Ile Leu Leu
1                5
```

( 2 ) INFORMATION FOR SEQ ID NO:30:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Ser Thr Leu Arg Val Leu Leu
1                5
```

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Ser Thr Val Arg Ile Leu Leu
1                5
```

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
Ser  Thr  Ala  Asn  Val  Leu  Leu
1                   5
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Leu  Thr  Gly  Glu  Leu  Leu  Thr  Leu  Ala
1                   5
```

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
Leu  Thr  Ala  Asp  Leu  Ile  Ser  Leu  Ala
1                   5
```

( 2 ) INFORMATION FOR SEQ ID NO:35:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
Leu  Thr  Ala  Pro  Thr  Phe  Thr  Leu  Ala
1                   5
```

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
Leu  Thr  Gly  Pro  Ser  Val  Ala  Leu  Ala
1                   5
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
Leu  Thr  Asp  Arg  Gln  Arg  Ala  Leu  Ala
1                       5
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Leu  Thr  Ala  Ser  Ser  Val  Thr  Leu  Ala
1                       5
```

( 2 ) INFORMATION FOR SEQ ID NO:39:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Leu  Thr  Ala  Arg  Pro  Gln  Thr  Leu  Ala
1                       5
```

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Leu  Thr  Val  Tyr  His  Arg  Glu  Leu  Ala
1                       5
```

( 2 ) INFORMATION FOR SEQ ID NO:41:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Leu  Thr  Ala  Pro  Gly  Thr  Ala  Leu  Ala
1                       5
```

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Leu  Thr  Ala  Leu  Gly  Arg  Asp  Leu  Ala
1                  5
```

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Leu  Thr  Ala  Arg  Ser  Ser  Gly  Leu  Ala
1                  5
```

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Leu  Thr  Gly  Phe  Arg  Arg  Lys  Leu  Ala
1                  5
```

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Asp  Ala  Glu  Asp  Gln  Leu  Gly  Ala  Arg  Val
1                  5                       10
```

(2) INFORMATION FOR SEQ ID NO:46:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Asp  Ala  Ala  Ala  Leu  Leu  Lys  Ala  Arg  Val
1                  5                       10
```

( 2 ) INFORMATION FOR SEQ ID NO:47:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Asp Ala Ala Ser Ala Leu Ala Ala Arg Val
1               5                   10
```

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Asp Ala Glu Leu Gly Asn Gln Arg Val
1               5
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Asp Ala Glu Arg Tyr Thr Gln Ser Arg Val
1               5                   10
```

( 2 ) INFORMATION FOR SEQ ID NO:50:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Asp Ala Asp Ser Phe Glu Glu Thr Arg Val
1               5                   10
```

( 2 ) INFORMATION FOR SEQ ID NO:51:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Asp Ala Ala Ser Leu Met Arg Gly Arg Val
1               5                   10
```

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Asp Ala Ala Gly Gly Arg Phe Gly Arg Val
1               5                   10
```

( 2 ) INFORMATION FOR SEQ ID NO:53:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

```
Asp Ala Ala Ile Cys Gly Gly Arg Val
1               5
```

( 2 ) INFORMATION FOR SEQ ID NO:54:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

```
Asp Ala Glu Val Phe Thr Asn Glu Arg Val
1               5                   10
```

( 2 ) INFORMATION FOR SEQ ID NO:55:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
Asp Ala Asp Arg Asn Gly Gln Leu Arg Val
1               5                   10
```

( 2 ) INFORMATION FOR SEQ ID NO:56:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Asp Ala Asp Val Gln Asn Glu Thr Arg Val
1               5                   10
```

( 2 ) INFORMATION FOR SEQ ID NO:57:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Asp Ala Asp Cys Ile Ala Ser Gly Arg Val
 1               5                   10
```

( 2 ) INFORMATION FOR SEQ ID NO:58:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Asp Ala Ala Val Val Lys Gly Gln Arg Val
 1               5                   10
```

( 2 ) INFORMATION FOR SEQ ID NO:59:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
Asp Ala Ala Ser Phe Lys Gly Glu Arg Val
 1               5                   10
```

( 2 ) INFORMATION FOR SEQ ID NO:60:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
Asp Ala Ala Phe Cys His Pro Gly Arg Val
 1               5                   10
```

( 2 ) INFORMATION FOR SEQ ID NO:61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

```
Asp Ala Val Leu Ser Gly Leu Thr Arg Val
 1               5                   10
```

(2) INFORMATION FOR SEQ ID NO:62:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

```
Asp Ala Ala Leu Pro Thr Asp Lys Arg Val
1               5                   10
```

(2) INFORMATION FOR SEQ ID NO:63:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

```
Asp Ala Val Trp Ser Ile Asp Arg Arg Val
1               5                   10
```

(2) INFORMATION FOR SEQ ID NO:64:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Asp Ala Val Ser Ser Glu Arg Lys Arg Val
1               5                   10
```

(2) INFORMATION FOR SEQ ID NO:65:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

```
Asp Ala Val Phe Glu Gly Asn Arg Arg Val
1               5                   10
```

(2) INFORMATION FOR SEQ ID NO:66:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

```
Asp Ala Ala Ser Leu Arg Gly Lys Arg Val
1               5                   10
```

( 2 ) INFORMATION FOR SEQ ID NO:67:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:67:

```
Asp Ala Ala Val Val Arg Leu Lys Arg Val
1               5                   10
```

( 2 ) INFORMATION FOR SEQ ID NO:68:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:68:

```
Asp Ala Ala Leu Arg Thr His Lys Arg Val
1               5                   10
```

( 2 ) INFORMATION FOR SEQ ID NO:69:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:69:

```
Asp Lys Ser Gly Ala Gly Glu
1               5
```

( 2 ) INFORMATION FOR SEQ ID NO:70:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:70:

```
Asp Lys Ser Gly Asn Gly Glu
1               5
```

( 2 ) INFORMATION FOR SEQ ID NO:71:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:71:

```
Asp Lys Ser Gly Ser Gly Glu
1               5
```

( 2 ) INFORMATION FOR SEQ ID NO:72:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

Gly Ala Gly Glu Arg Gly Ser
1               5

( 2 ) INFORMATION FOR SEQ ID NO:73:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

Gly Ala Gly Tyr Asp Gly Ser
1               5

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

Gly Ala Gly Arg His Gly Ser
1               5

( 2 ) INFORMATION FOR SEQ ID NO:75:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

Gly Ala Gly Gln Pro Gly Ser
1               5

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

Gly Ala Cys Pro Gly Ser
1               5

( 2 ) INFORMATION FOR SEQ ID NO:77:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

```
Gly Ala Ser Lys Asp Gly Ser
1               5
```

( 2 ) INFORMATION FOR SEQ ID NO:78:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Gly Ala Cys Asp Ser Gly Ser
1               5
```

( 2 ) INFORMATION FOR SEQ ID NO:79:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Gly Ala Ser Lys Arg Gly Ser
1               5
```

( 2 ) INFORMATION FOR SEQ ID NO:80:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Gly Ala Ser Ser Pro Gly Ser
1               5
```

( 2 ) INFORMATION FOR SEQ ID NO:81:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

```
Gly Ala Cys Tyr Asn Gly Ser
1               5
```

( 2 ) INFORMATION FOR SEQ ID NO:82:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:82:

Gly Ala Cys Asn Ser Gly Ser
1               5

( 2 ) INFORMATION FOR SEQ ID NO:83:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:83:

Gly Ala Ser Glu Asn Gly Ser
1               5

( 2 ) INFORMATION FOR SEQ ID NO:84:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:84:

Gly Ala Leu Glu Tyr Gly Ser
1               5

( 2 ) INFORMATION FOR SEQ ID NO:85:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:85:

Gly Ala Leu Arg His Gly Ser
1               5

( 2 ) INFORMATION FOR SEQ ID NO:86:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear (ii) MOLECULE TYPE: peptide (xi) SEQUENCE DESCRIPTION: SEQ ID NO:86:

Gly Ala Val Gln Pro Gly Ser
1               5

# METHODS FOR MODIFYING DNA AND FOR DETECTING EFFECTS OF SUCH MODIFICATION ON INTERACTION OF ENCODED MODIFIED POLYPEPTIDES WITH TARGET SUBSTRATES

This is a continuation of application Ser. No. 08/039,501 filed Mar. 29, 1993, now abandoned, which is a continuation of application Ser. No. 07/602,158 filed Oct. 22, 1990, now abandoned.

TECHNICAL FIELD OF THE INVENTION

The invention relates to methods and mutation linkers to modify DNA, to methods for producing libraries containing a multiplicity of modified DNA, and to methods for using such libraries for screening modified proteins encoded by such DNA.

BACKGROUND OF THE INVENTION

There are two common ways to identify domains and specific amino acid residues within a polypeptide that are important for its structure and function. One approach is to compare the amino acid sequences of a family of naturally occurring polypeptide variants which are homologous and perform the same or similar function. Those residue positions which are conserved are assumed to be crucial to the structure and activity of each of the polypeptides within that family. This approach has been used for a number of proteins including the globin family (Bashford, D., et al., (1987), *J. Mol. Biol.*, 196:199–216; Lesk, A. M., et al., (1980), *J. Mol. Biol.*, 136:225–235). The second approach is to probe the importance of regions of a polypeptide by changing or deleting individual amino acids or a group of amino acid residues and examining the functional consequences. Examples of this approach include random mutagenesis of the lac repressor (Miller, J. H., et al., (1979), *J. Mol. Biol.*, 131:191–200) and Staphylococcal nuclease (Shortle, D., et al., (1985), *Genetics*, 110:539–555), systematic site-specific mutagenesis such as "alanine-scanning" mutagenesis of hGH (Cunningham, B. C., et al., (1989), *Biochemistry*, 28:5703–5707), and by "segment substitution" of hGH with homolog segments (Cunningham, B. C., et al., (1989), *Science* 243:1330–1336).

The mutagenesis approach offers the advantage that analysis is not limited to existing natural variants. However, most random mutagenesis experiments depend on the generation of point mutations. Since codons contain three nucleotides, it is generally not possible to sample all of the nineteen other amino acids at a residue position with point mutations. This results in a bias when assessing the tolerance of a residue to different amino acid substitutions.

A third approach has recently been described called "combinatorial cassette mutagenesis" or simply "cassette mutagenesis (Kaiser, C. A., et al., (1987), *Science*, 235:312–317; Reidhaar-Olson, J. F., et al., (1988), *Science*, 241:53–57). The method typically involves substituting a DNA segment between two restriction sites with a cassette containing one or more codons which have been completely randomized so that they encode all possible amino acid residues. Cassette mutagenesis has been used to study signal sequences (Kaiser, et al., supra), the dimer interface, two α-helices and the hydrophobic core of λ repressor (Reidhaar-Olson, et al., supra; Reidhaar-Olson, J. F., et al., (1990), *Proteins Struc. Funct. Genet.*, 7:306–316; Lim, et al., (1989) *Nature (London)*, 339:31–36), a region around the catalytic serine residue of TEM β-lactamase (Dube and Loeb, 1989), *Biochemistry* 2: 5703–5707, and proteases such as subtilisin (EPO Publication No. 0 251 446 published Jun. 7, 1988).

The technique of linker insertion mutagenesis was reported by Heffron, F., et al., (1978), *Proc. Natl. Acad. Sci. USA*, 75:6012–6016. In this method, a linker encoding a single synthetic restriction site is inserted into DNA at random sites, followed by digestion with an enzyme cognate for that synthetic site to map the point of insertion. This technique can lead to net additions to the target DNA comprising the synthetic restriction site nucleotides plus any additional nucleotides included in the linker. Alternatively, this technique can lead to substitution or net deletion depending on the number of nucleotides removed from the target DNA after the initial DNaseI digestion step and prior to linker insertion. Regardless of the net change in size of the target DNA, this method forces the inclusion in the mutant genome of base-pairs encoding the added restriction site.

Another approach, known as "linker scanning mutagenesis" (McKnight, S. L., et al., (1982), *Science*, 217:316–324), begins with libraries carrying mutations created according to the above linker insertion technique. Mutations are mapped and then cleaved at the added synthetic restriction sites to form mutant DNA fragments. Appropriate mutant fragments which are 5' and 3' of the synthetic restriction site and each encoding part of the added restriction site are then ligated together to form mutated DNA bearing substitutions, additions or deletions engineered according to the linker insertion technique. Of course, these mutations also necessarily encode the added synthetic restriction site.

Bidirectionally cleaving excision linkers encoding two BspMI recognition sequences have reportedly been inserted into ScaI cleaved pBR322 and thereafter cleaved with BspMI. The ends of the resultant DNA are then treated with either exonuclease or DNA polymerase to remove or fill in nucleotides. This reportedly results in the deletion of 2 to 16 nucleotides depending on the location of the recognition sequence for BspMI in the excision linker and the location of the cleavage site for those recognition sequences near the ScaI insertion site (Mormeneo, S., et al., (1987), *Gene*, 61:21–30). Also suggested is a scheme to delete 3 nucleotides while substituting one nucleotide as well as a suggestion to use a bidirectionally cleaving linker wherein equal numbers of nucleotides are removed on one side of the linker and added to the other side. Such substitution, however, is necessarily limited to the number of nucleotides between the recognition sequence and cleavage site of the Class IIS endonuclease. Further, in each case, only one bidirectionally cleaving linker is used to obtain the final product.

It is an object of the invention to provide improved methods for modifying DNA whereby the modification includes the substitution of one or more nucleotides with predetermined or random nucleotides throughout a target DNA or at a predetermined site within said target DNA.

It is a further object of the invention to provide novel vectors encoding the modified DNA made according to the methods of the invention.

Still further, it is an object of the invention to provide transformed cells which express modified polypeptides encoded by the DNA modified by the methods of the invention.

More particularly, it is an object herein to provide cell populations transformed by the above methods to express modified forms of β-lactamase with random mutations throughout or at predetermined sites within the β-lactamase} gene, to screen antibiotics for susceptibility to hydrolysis by the modified lactamases expressed by such cell populations.

The references discussed above are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the above objects, methods are provided for modifying target DNA. In specific embodiments such modified target DNA encodes modified polypeptides. The desired substitutions, insertions or deletions of nucleotide are preferably introduced into the target DNA through the sequential (1) insertion and removal of a bidirectionally cleaving Class IIS excision linker to remove target nucleotides, by (2) insertion and removal of a bidirectionally cleaving Class IIS mutation linker to add mutation nucleotides, and (3) ligation to form modified target DNA.

Central to the invention is the design of the excision and mutation linkers such that the desired DNA modifications are produced. To this end, the bidirectionally cleaving excision linker comprises two recognition sequences for Class IIS restriction endonucleases, one at or near each end of the excision linker. Typically, a variable number of spacer nucleotide base-pairs is incorporated between the two Class IIS recognition sequences. The two Class IIS recognition sequences are oriented and positioned such that the cleavage sites for cognate Class IIS restriction endonuclease do not lie within the excision linker itself. Rather, once the excision linker is inserted into the target DNA, to form a first modified DNA, the cleavage sites lie within first and second portions of the target DNA on either side of the excision linker insertion site. The exact location of the cleavage site is determined by the type of Class IIS endonuclease used and the position of the recognition sequences in the excision linker. If the excision linker is inserted randomly throughout the target DNA, the subsequent steps result in the modification of one or more nucleotides throughout the target DNA. The excision linker, however, can be inserted at a predetermined site in the target DNA so that modification of the nucleotide sequence in the target DNA occurs at a predetermined site.

After insertion of the excision linker into the target DNA, the first modified DNA so formed is cleaved with cognate Class IIS restriction endonuclease. This produces a second modified DNA containing either blunt or staggered ends, depending on the specific Class IIS restriction endonuclease encoded by each recognition sequence in the excision linker. Since the cleavage site for each Class IIS endonuolease recognition sequence is located within the first and second DNA portions contained in the first modified DNA, digestion with Class IIS restriction endonucleases removes one or more nucleotides from the target DNA generally on each side of the insertion site of the excision linker to form third and fourth DNA portions.

If blunt end Class IIS restriction endonuclease recognition sequences are encoded at both ends of the excision linker, the number of nucleotides removed from each end of the first and second DNA portions to form third and fourth DNA portions is determined by the position of the cleavage sites in the first and second DNA portions. If a recognition sequence for a Class IIS restriction endonuclease which produces staggered ends is encoded, such ends are modified by exonuclease or DNA polymerase treatment to form modified third and forth DNA portions which contain blunt ends.

The blunt ends of the third and fourth DNA portions are then ligated with a bidirectionally cleaving mutation linker to form third modified DNA. The mutation linker encodes two Class IIS recognition sequences and one or more mutation nucleotides contained within a mutation nucleotide end region located at each end of the mutation linker. As with the excision linker, the Class IIS recognition sequences are orientated so that cleavage by cognate Class IIS endonuclease does not occur between the recognition sequences. The recognition sequences, however, are positioned so that the mutation end nucleotide regions are cleaved from the mutation linker when digested with cognate Class IIS endonuclease. As a consequence, when the third modified DNA is cleaved with cognate Class IIS endonuclease to form fourth modified DNA, the nucleotides contained within each mutation nucleotide end region remain covalently attached to third and fourth portions of the target DNA thereby forming fifth and sixth portions.

If the ends of the fifth and sixth portions contain staggered ends (as determined by the Class IIS endonuclease recognition sites encoded in the mutation linker), they are treated with exonuclease or DNA polymerase to produce blunt ends.

The blunt ends of the fifth and sixth positions of the target DNA are thereafter ligated to form the modified target DNA wherein one or more nucleotides have been substituted, inserted or deleted as compared to the original target DNA.

Substitution of one or more nucleotides occurs when the total number of nucleotides deleted by removal of the excision linker upon treatment with Class IIS endonuclease (and subsequent modification with exonuclease or DNA polymerase, if necessary) equals the number of nucleotides added by removal of part of the mutation linker by Class IIS endonuclease (and subsequent modification with exonuclease or DNA polymerase, if necessary). Net insertions or deletions are produced when the number of nucleotides removed and added are unequal.

In one aspect of the invention, the mutation linker is designed so that at least three random mutation nucleotides are located in the mutation nucleotide end regions so that target nucleotides in the target DNA are substituted with these random mutation nucleotides. When random nucleotides are incorporated into the modified target DNA and the target DNA encodes a polypeptide, the codons so modified potentially encode all possible amino acid substitutions.

Once the target DNA has been modified the effect of such modification is determined. In this aspect of the invention, the modified target DNA will generally encode one or more modified polypeptides. This occurs generally when the mutation linker encodes random mutation nucleotides and/or the excision linker is randomly inserted into the target DNA. When the modified target DNA is formed in an expression vector, appropriate cells may be transformed to form a library capable of expressing the modified polypeptides encoded by such modified target DNA. Such modified polypeptides may thereafter be analyzed to determine the effect of such modifications. In this aspect of the invention, the modified polypeptide is contacted with a target which normally interacts with the unmodified polypeptide. The interaction of one or more of the modified polypeptides with the target, if any, is determined. A change in the interaction between one or more of the modified polypeptides and the target as compared to the same interaction by the unmodified polypeptide coupled with the determination of the amino acid residue(s) modified in the polypeptide provides an indication of which amino acid residues in the unmodified or modified polypeptide interact with the target.

In a specific aspect of the invention, libraries of transformed cells encoding modified antibiotic hydrolases, such as modified β-lactamases, are used to determine the susceptibility of an antibiotic to neutralization by wild-type mutants of the antibiotic hydrolases. Such libraries preferably contain the substitution of discrete regions of the antibotic hydrolase. Such regions are preferably within the active site of the enzymes that are involved in catalysis, binding and\or specificity of the enzyme with the antibiotic substrate. Generally, such libraries encode substantially all of the combinations of substitutions that can be made among the amino acid residues within each region modified. As a consequence, such libraries, alone or in combination with other libraries, provide a repertoire of modified antibiotic hydrolases that are representative of the various mutations which may occur in the wild-type antibiotic hydrolase. The susceptibility of the particular antibiotic to neutralization by any one of the modified antibiotic hydrolases in the library provides an indication of its susceptibility to neutralization by wild-type mutations in the precursor antibiotic hydrolase.

The invention also includes bidirectionally cleaving mutation linkers useful in practicing the methods of the invention, compositions comprising modified DNAs and modified polypeptides made according to the methods of the invention, cell populations transformed with modified target DNA as well as novel methods for site directed insertion of the excision linker used in practicing the methods of the invention.

BRIEF DESCRIPTION OF THE DRAWINGS

FIG. 1 depicts the relationship between the excision linker and first and second DNA portions when inserted into target DNA.

FIG. 1A shows the cleavage site (SEQ ID NO:1) for blunt end cleaving Class IIS endonuclease.

FIG. 1B shows the cleavage site (SEQ ID NO:2) for a Class IIS endonuclease that produces staggered ends.

FIG. 2 summarizes the abbreviations used in FIGS. 2A through 2H.

FIGS. 2A through 2H schematically depict the method of the invention using a Class IIS restriction endonuclease that cleaves to form blunt ends.

FIG. 3 depicts the insertion site of an excision linker in linear or plasmid target DNA.

FIGS. 3A through 3G schematically depict the method of the invention using a Class IIS restriction endonuclease that cleaves to form staggered ends.

FIG. 4 defines some of the abbreviations in FIGS. 4A through 4E.

FIGS. 4A through 4E schematically depict an embodiment utilizing PCR-mediated site directed insertion of an excision linker into target DNA.

FIG. 5 defines portions depicied in FIGS. 5A through 5G.

FIGS. 5A through 5G depict the modification of a region of the β-lactamase gene using excision and mutation linkers with recognition sequences for the Class IIS restriction endonuclease, BspMI.

FIGS. 6A through 6J depicts the PCR method of site-directed linker insertion used to generate blaC66 mutants (SEQ ID NO:3).

FIG. 7 depicts the nucleotide (SEQ ID NO: 15) and amino acid sequence (SEQ ID NO: 16) of the bla gene and the positions of insertions of the BspMI excision linker. The arrows indicate the insertion points of the linkers. The boxed nucleotides indicate the nucleotides which were randomized. Those inserts with two arrows represent deletions associated with the BspMI linker insertion. The nucleotides between the arrows were deleted and replaced also with random nucleotides.

FIG. 8 depicts the percent of functionally acceptable replacement mutants at 10 µg/ml and 1 mg/ml ampicillin versus the residue positions modified. Each set of bars indicates a separate random replacement experiment.

FIG. 9 depicts the amino acid sequences for the blaC66 replacement experiment of residues 72–74. The sequence of wild type TEM β-lactamase is at top (SEQ ID NO: 17) followed by 1 mg/ml and 10 µg/ml functional replacement mutants (SEQ ID NOS: 18–32).

FIG. 10 depicts the amino acid sequences for the blaC31 replacement experiment of residues 196–200. The sequence of wild type TEM β-lactamase is at top (SEQ ID NO: 33) followed by 1 mg/ml and 10 µg/ml functional replacement mutants (SEQ ID NOS: 34–44).

FIG. 11 depicts the amino acid sequences for the blaC14 replacement experiment of residues 37–42. The sequence of wild type TEM β-lactamase is at top (SEQ ID NO: 45) followed by 1 mg/ml and 10 µg/ml functional replacement mutants (SEQ ID NOS: 46–61). The sequence of nonfunctional mutants is at bottom (SEQ ID NOS: 62–68).

FIG. 12A depicts the percent of functionally acceptable replacement mutants at 1 mg/ml ampicillin versus the residue positions mutagenized. FIG. 12B depicts the average evolutionary variability for the equivalent residue positions in FIG. 12A.

FIG. 13 depicts the position of active-site libraries within the bla gene (SEQ ID NOS: 15 and 16). The boxed nucleotides indicate the nucleotides which were randomized in each library.

FIG. 14 depicts the position of the active-site libraries within the three-dimensional structure of the homologous class A β-lactamase from S. aureus. The darkened regions correspond to the amino acid positions randomized in the libraries. The identity of each library is indicated by arrows. The position of the catalytic serine residue within the active-site is also shown (Figure adapted from Hertzberg, O., et al., (1987), Science, 23:694–701).

FIG. 15 depicts the amino acid sequences for the blaC71 library at positions 235–237. The sequence of the wild type TEM-1 β-lactamase is at top (SEQ ID NO:69) followed by mutants (SEQ ID NOS: 70 and 71) with the indicated substrate specificities.

FIG. 16 depicts the amino acid sequences for the blaC74 library at positions 238–241. The sequence of the wild type TEM-1 β-lactamase is at top (SEQ ID NO followed by mutants (SEQ ID NOS: 73–86) with the indicated substrate specificities.

DETAILED DESCRIPTION OF THE INVENTION

The methods of the invention are used to modify target DNA. When the target DNA encodes a precursor polypeptide, the target DNA is typically modified to substitute a multiplicity of target nucleotides with random mutation nucleotides. The modified target DNA so formed is generally used to produce libraries of transformed cells capable of expressing the modified DNA to produce modified polypeptides. More particularly, such libraries are useful in the rational design and screening of new drugs. For example, neutralization of one or more antibiotics by modified β-lactamases within a library made according to the invention coupled with the determination of the modified β-lactamase sequence can provide useful information which can be used to design antibiotics which resist neutralization by naturally occurring β-lactamase mutants. Additionally, antibiotic drug candidates can be screened against such libraries to predict the likelihood that the antibiotic will be susceptible to neutralization by natural mutations of the β-lactamase gene. Other uses for the invention disclosed herein will be apparent from the following detailed description.

The methods of the invention rely upon the unique properties of Class-IIS restriction endonucleases. As used herein, a "Class IIS restriction endonuclease" or "Class IIS endonuclease" is an enzyme that recognizes a non-palindromic double stranded nucleotide sequence and cleaves both strands at a precise distance from the recognition sequence (Szbalski, W. (1985), Gene, 40:169–17). Examples of the recognition sequences and cleavage sites of typical Class-IIS restriction endonucleases are schematically diagrammed in FIG. 1. As shown in FIG. 1A, the 5' and 3' strand cleavage sites for MnlI are both seven nucleotides from and on the same side of the recognition sequence (SEQ ID NO:1). This results in blunt end cleavage of the double-stranded DNA seven nucleotides from the recognition sequence. Most Class IIS restriction endonucleases cleave on the same side of the recognition sequence but at different distances for the 5' and 3' strands. Thus, for example, as shown in FIG. 1B, BspMI cleaves the 5' strand 4 nucleotides and the 3' strand 8 nucleotides from the BspMI recognition sequence (SEQ ID NO: 2) to produce staggered ends. There are to date 13 class-IIS restriction endonucleases which have been described (Table I), 12 of which produce staggered ends upon cleavage, and one of which produces blunt ends. As will be apparent, the invention is not limited to the specific Class IIS enzyme used in the preferred embodiment or to the known Class IIS enzymes of Table I. Rather, any Class IIS restriction endonuclease defined functionally as a restriction endonuclease which cleaves outside the recognition sequence for that enzyme can be used to practice the invention. Such enzymes are or will be apparent to one skilled in the art since the determination of recognition sites and cleavage sites for restriction endonucleases is routine.

TABLE I

| Enzyme | Recognition Sequence and Cleavage Site |
|---|---|
| BvbI | 5' - GCAGCN$_8$↓ |
|  | 3' - CGTCGN$_{12}$↓ |
| BbvII | 5' - GAAGACN$_2$ |
|  | 3' - CTTCTGN$_6$ |
| BinI | 5' - GGATCN$_4$ |
|  | 3' - CCTAGN$_5$ |
| FokI | 5' - GGATGN$_9$ |
|  | 3' - CCTACN$_{13}$ |
| HgaI | 5' - GCGCN$_5$ |
|  | 3' - CTGCGN$_{10}$ |
| HphI | 5' - GGTGAN$_8$ |
|  | 3' - CCACTN$_7$ |
| MboII | 5' - GAAGAN$_8$ |
|  | 3' - CTTCTN$_7$ |
| MnlI | 5' - CCTCN$_7$ |
|  | 3' - GGAGN$_7$ |
| SfaNI | 5' - GCATCN$_5$ |
|  | 3' - CGTAGN$_9$ |

TABLE I-continued

| Enzyme | Recognition Sequence and Cleavage Site |
|---|---|
| TaqII | G   G |
|  | 5' - CACCCAN$_{11}$ |
|  | 3' - CTGGCTN$_9$ |
|  | G   G |
| TthIIII | 5' - CAAPuCAN$_{11}$ |
|  | 3' - GTTPyGTN$_9$ |
| BspMI | 5' - ACCTGG(N)$_4$ |
|  | 3' - TGGACG(N)$_8$ |
| PleI | 5' - GAGTC(N$_4$) |
|  | 3' - CTCAG(N$_5$) |

The methods of the invention are used to modify the DNA sequence of "target DNA". In general, any DNA sequence may be modified by the methods of the invention. Generally, all that is required is that the target DNA be contained within a replicable vector which is capable of being manipulated according to the steps of the invention. Thus, although specific embodiments disclosed herein describe the modification of codons contained within the structural portion of a precursor gene, target DNA is not limited to such new DNA sequences. Thus, DNA sequences such as expression regulation sequences, introns, enhancer sequences and the like may be modified according to the invention. In the embodiments disclosed herein, the target DNA preferably encodes a precursor polypeptide. When one or more nucleotides contained within the target DNA is modified according to the invention, the "modified target DNA" encodes a "modified polypeptide" wherein one or more adjacent codons have been modified to encode a different amino acid residue from that of the precursor polypeptide. The methods disclosed herein, however, can also be used in subsequent cycles whereby the modified target DNA product of one round of mutagenesis becomes the target DNA for another round of mutagenesis.

Examples of the precursor polypeptides which may be modified by the methods of the invention include enzymes, proteinaceous hormones, proteinaceous receptors, structural proteins, and regulatory proteins. Specific classes of enzymes include antibiotic detoxifying enzymes such as TEM β-lactamases of Classes A, B, C, and D, and chloramphenicol acetyl transferase, carbonyl hydrolases such as the serine and carboxyl proteases, e.g. subtilisin, trypsin, chymotrypsin, carboxy peptidase and the like, lipases such as phospholipase A, lipoprotein lipase, pancreatic lipase, and lysosomal lipase, endo and exoglycosidases such as endoglycosidase H, nucleases including exonucleases DNAse I (human) and RNAse A, endonucleases such as EcoRI and BamHI, detoxifying enzymes such as catalase, peroxidase, and superoxide dismutase, and protein kinases such as protein kinase C. Examples of proteinaceous hormones include growth hormones, e.g. human growth hormone and bovine growth hormone, and proteinaceous hormone receptors such as the somatogenic and diabetogenic receptors for growth hormone. Other important receptors include the G-protein coupled receptors such as the B-adrenergic and muscarinic receptors. Examples of structural proteins which may be modified by the methods of the invention include collagen, myosin, tubulin and actin. The foregoing is merely suggestive of the types of precursor polypeptides which may be modified by the invention.

Once a particular precursor polypeptide is chosen for modification, the DNA encoding the chosen polypeptide is generally isolated and cloned into a vector capable of replication and selection in the microorganism chosen for use in practicing the invention. Generally procaryotic organisms such as *E. coli*, Bacillus, Salmonella, and simple eukaryotes such as the yeast Sacharomyces are used for cloning and modifying of the target DNA and an appropriate vector will be used for each particular cloning host. Proteins can also be directly expressed in more complex eukaryotic animal cells. Such organisms and vectors are well known to those skilled in the art.

In many cases, it will be desirable to clone the target DNA encoding a polypeptide in an expressible form so as to analyze the modified polypeptide encoded by modified target DNA. Depending upon the particular precursor polypeptide chosen for modification and the host to be used for cloning and/or expression, replicable expression vectors capable of expressing the target DNA and modified target DNA can be readily selected by those skilled in the art. When cloning and modifications do occur in one cell type following by expression in another, e.g. procaryotic cloning and modification followed by expression in eucaryotic cells, e.g. tissue culture and the like, appropriate shuttle vectors can be constructed by those skilled in the art. Alternatively, a DNA cassette containing the target DNA can be inserted into a replicable vector, modified and thereafter removed and inserted into an appropriate vector for expression of the modified polypeptide.

Once the target DNA has been selected and cloned, various modifications may be made to the target DNA sequence by the methods of the invention. Depending upon the structure of the excision linker and mutation linker as described in more detail hereinafter, the method of the invention produces the substitution, insertion or deletion of one or more target nucleotides in the target DNA. When the target DNA comprises codons, it is possible to substitute one or more target nucleotides such that a predetermined modification of one or more codons occurs. Thus, for example, to the extent it is desirable to produce substantially all possible amino acid substitutions at one or more adjacent codons within one or more regions comprising all or part of the active site of an enzyme, excision and mutation linkers are chosen which substitute the target nucleotides of one or more adjacent predetermined codons within each region with random mutation nucleotides. Alternatively, the target nucleotides of one or more adjacent codons throughout a target DNA can be substituted with random mutation nucleotides. As will be described in more detail, random integration of the excision linker of the invention into target DNA results in random modification of target nucleotides in the target DNA. Modification of predetermined target nucleotides, however, occurs when the excision linker is introduced into the target DNA at a predetermined insertion site within or adjacent to the target nucleotide to be modified. As described in more detail hereinafter, an exquisitely simple and powerful method using the polymerase chain reaction (PCR) is disclosed which facilitates excision linker insertion at a predetermined site in the target DNA.

FIG. 2 depicts an embodiment of the invention wherein all Class IIS endonuclease products are blunt ended upon cleavage. As indicated in FIG. 2A, target DNA comprises two portions, a first DNA portion and a second DNA portion separated by the insertion site of an excision linker. In the first step of the method, an "excision linker" is introduced into the target DNA either randomly at any point in the target DNA or at a predetermined insertion site. The excision linker is used to "excise" target nucleotides from the target DNA and comprises doubled-stranded DNA which encodes a first recognition sequence and a second recognition sequence for the same or two different Class IIS restriction endonucleases (FIG. 2B). The recognition sequences (R) are located at or near each end of the excision linker and are oriented such that the cognate Class IIS restriction endonuclease for each recognition sequence does not cleave between the two recognition sequences (FIG. 2B). The arrowhead next to R in the excision linker in FIG. 2 points in the direction of the cleavage site encoded by each recognition sequence. Typically, several spacer nucleotides are located between the two recognition sequences to increase the efficiency of subsequent removal of the excision linker. In addition, various markers and/or selection characteristics may be encoded between the recognition sequences such as restriction sites to facilitate the determination of the site of excision linker insertion or the selection of successful transformants containing the excision linker. In most cases, the recognition sequence for each Class IIS nuclease will be located at each terminus of the excision linker. However, in some applications, the recognition sequence may be set back one or more nucleotides from the terminus of the excision linker. When so positioned, modification of the number of target nucleotides removed in subsequent steps may be obtained. The positioning of one or more of the recognition sequences away from the terminus of the excision linker may be desirable, for example, when the excision linker is inserted at a predetermined site and only target nucleotides of predetermined codons of a target DNA are to be modified. Such variation in recognition sequence positioning will be apparent to one skilled in the art following the teachings of the application. As used herein, the terms "excision linker" and "bidirectionally cleaving excision linker" refer to DNA having the aforementioned structure.

Insertion of the excision linker into the insertion site of the target DNA forms a first modified DNA comprising the first DNA portion, the excision linker and the second DNA portion (FIG. 2C). When so inserted, the first and second recognition sequences of the excision linker encode first and second cleavage sites respectively in the first and second DNA portions of the first modified DNA. Those nucleotides of the target DNA contained between each cleavage site and the site of excision linker insertion comprise first and second target nucleotide end regions (referred to as first and second TNERs). It is these target nucleotides which are removed from the target DNA by the methods of the invention.

Digestion of the first modified DNA with cognate Class IIS restriction endonuclease for each recognition sequence produces second modified DNA comprising third and fourth DNA portions. These third and fourth portions correspond to the first and second DNA portions except that the target nucleotides of each TNER are removed. As indicated in FIG. 2d, the target nucleotides of each TNER are removed with the excision linker upon digestion. Thus, the third DNA portion corresponds to the first DNA portion minus target nucleotide $N_1$ through $N_X$. Similarly, the fourth DNA portion corresponds to the second DNA portion minus target nucleotides $N_Y$ through $N_Z$. Although the specific embodiment disclosed removes target nucleotides from both the first and second DNA portions, it is be to be understood that it is possible to remove target nucleotides from only one of either the first or second DNA portions using the method of the invention.

A "mutation linker" (sometimes referred to as a "bidirectionally cleaving mutation linker") (FIG. 2E) is then ligated to the ends of the third and fourth portions of the second modified DNA to form a third modified DNA (FIG. 2F). Like the excision linker described above, the mutation linker encodes two recognition sequences for the same or two different Class IIS restriction endonucleases (FIG. 2E). These two recognition sequences (sometimes referred to as third and fourth recognition sequences), however, are oriented and positioned in the mutation linker so that a cleavage site (sometimes referred to as third and fourth cleavage sites) is located between each recognition sequence and the end of the mutation linker as shown in FIG. 2E. Those nucleotides between each of the cleavage sites and the end of the mutation linker are referred to as "mutation nucleotides" and comprise "mutation nucleotide end regions" (MNERs) of the mutation linker. As will be clear from the following discussion relating to the use of Class IIS endonucleases which produce staggered cleavage ends, all or some of the mutation nucleotides contained within one or both mutation nucleotide end regions are incorporated into the modified target DNA. When so constructed, the mutation nucleotide end region at each end of the mutation linker contains mutation nucleotides $M_1$ through $M_x$ and $M_y$ through $M_z$. Such mutation nucleotides may be predetermined, i.e., comprise a predetermined sequence or may comprise one or more random nucleotides. Depending upon the particular type of Class IIS endonuclease encoded by the third and fourth recognition sequences, spacer nucleotides $S_1$ through $S_n$ are incorporated between each recognition sequence and mutation nucleotide end region so that the cleavage site for the cognate Class II endonuclease is properly positioned in the mutation linker. In the preferred embodiment, the region between the two recognition sequences may also encode a selectable marker, such as lacO, which is assayable by color, for determination of successful transformants containing the mutation linker and the measurement of library size.

After ligation of the mutation linker with the second modified DNA the third modified DNA so formed (FIG. 2F), is digested with cognate Class IIS restriction endonuclease to yield fourth modified DNA comprising fifth and sixth DNA portions (FIG. 2G). The fifth and sixth portions correspond to the third and fourth DNA portions except that the mutation nucleotides $M_1$ through $M_x$ and/or $M_y$ through $M_z$, formerly contained within the MNERs, have been added to the third and/or fourth DNA portions. The ends of the fifth and sixth portions are then ligated together to produce the modified target DNA wherein nucleotides $N_1$ through $N_x$ and/or $N_y$ through $N_z$ have been removed from the target DNA and mutation nucleotides $M_1$ through $M_x$ and/or $M_y$ through $M_z$ have been added.

As indicated, the foregoing description of the preferred method of the invention describes the use of recognition sequences which encode for blunt end cleavage sites for Class IIS endonucleases. When recognition sequences are used for Class IIS endonucleases which form staggered ends upon cleavage, the staggered ends so formed during removal of the excision linker and/or removal of the mutation linker may be further modified. Such modification is generally required in most instances to facilitate ligation. FIG. 3 depicts a preferred embodiment of the invention wherein each of the recognition sequences in the excision and mutation linkers encode for staggered Class IIS endonuclease cleavage. For illustrative purposes, FIG. 3 shows the use of a Class IIS endonuclease, the cleavage point of which lies six nucleotides 5' of and three nucleotides 3' of the end of its recognition site. To date, no Class IIS endonuclease has been described with this exact cleavage characteristic (see Table I, supra), however this example will serve to illustrate the principles of the method of the invention when staggered ends are produced by the particular Class IIS endonuclease utilized. As shown in FIG. 3, the nucleotides in the first cleavage site in the first modified DNA are designated $X_1$ through $X_6$ with corresponding paired nucleotides $X_1'$ through $X_6'$. Nucleotides $X_7$ through $X_{12}$ and complementary nucleotides $X_7'$ through $X_2'$ are similarly located about the second cleavage site. Upon cleavage with a Class IIS endonuclease, a third DNA portion is formed wherein nucleotides $X_1$, $X_2$ and $X_3$ form single stranded DNA. Similarly, a fourth DNA portion is formed with 3 nucleotides ($X_{10}$, $X_{11}$ and $X_{12}$) of single-stranded DNA on the end. One modification of the third and fourth portions comprises treating such DNA with an appropriate DNA polymerase such as the Klenow fragment of DNA polymerase I of E. coli in the presence of nucleotide triphosphates. Such treatment fills in the single stranded DNA with the appropriate matching base pair.

The modified third and fourth DNA portions so obtained are depicted in FIG. 3C by the paired bases

| $X_1'X_2'X_3'$ | | $X_{10}'X_{11}'X_{12}'$ |
|---|---|---|
| $X_1\ X_2\ X_3$ | and | $X_{10}\ X_{11}\ X_{12}$ |

The effect of such DNA polymerase treatment is to limit the nucleotides effectively removed by the excision linker to those target nucleotides defined by the cleavage site located closest to the excision linker.

Alternatively, the ends of the third and fourth DNA portions may be treated with a single-strand exonuclease to remove those nucleotides which are not base-paired. When so treated, $X_1$, $X_2$ $X_3$ and $X_{10}$, $X_{11}$, $X_{12}$ are removed and the maximum number of target nucleotides are removed from the target DNA. For example, if an excision linker containing two BspMI recognition sequences positioned at the end of the linker is used, the first modified target DNA shown in FIG. 1B is produced. Upon digestion with BspMI four target nucleotides from one strand and eight target nucleotides from the other strand of the first and second DNA portions are removed with the excision linker. If the ends of the first and second DNA portions are treated with the DNA polymerase, the net removal from the target DNA is four nucleotides on each side of the insertion site. If, however, the first and second DNA portions are treated with exonuclease, a total of eight nucleotides from each side of the insertion site are removed. Thus, using BspMI, depending upon the method of modification, a total of eight or 16 nucleotides may be removed during the preliminary steps of the method of the invention.

Similarly, when the mutation linker encodes staggered end cleavage by Class IIS endonuclease, the third and fourth cleavage sites within the mutation linker have a cleavage site schematically set forth in FIG. 3 for mutation nucleotides $M_1$ through $M_6$ and $M_7$ through $M_{12}$ with corresponding base pair mutation nucleotides $M_1'$ through $M_6'$ and $M_7'$ through $M_{12}'$. As can be seen, when the mutation linker is ligated to the third and fourth (or third and fourth modified portions) and the third modified DNA so formrf digested with cognate Class IIS endonuclease, the fifth and sixth DNA portions shown in FIG. 3(e) are obtained. As can be seen, nucleotides $M_1$, $M_2$, $M_3$ and $M_{10'}$, $M'_{11}$, $M'_{12}$ are single stranded. These ends can be treated with DNA polymerase to fill in the single stranded mutation nucleotides $M'_1$, $M'_2$, $M'_3$ and $M_{10}$, $M_{11}$, and $M_{12}$. When filled in, the maximum number of mutation nucleotides is introduced into the target DNA. When single strand bases are removed by exonuclease treatment, fewer mutation nucleotides for the particular Class IIS endonuclease are introduced into the target DNA. Similarly, when BspMI cleavage is encoded by both the third and fourth recognition sequences of the mutation linker, a maximum of 16 and minimum of 8 mutation nucleotides are added by the mutation linker depending upon the modification step used.

As used herein, the term "substitution" refers to one for one replacement of one or more target nucleotides of the target DNA with the same number of random or predetermined mutation nucleotides. In other words, the number of target nucleotides removed by the excision linker equals the number of mutation nucleotides added by the mutation linker. The term "insertion" indicates that more mutation nucleotides have been added by the mutation linker than removed by the excision linker. Similarly, the term "deletion" indicates that the number of nucleotides removed by the excision linker is greater than the number of nucleotides added by the mutation linker.

It is understood that this technique may be modified to utilize combinations of different Class IIS restriction endonuclease. For instance, the excision linker (FIG. 2B) may be designed with recognition sequences for Class IIS restriction endonucleases which produce staggered cleavage while the Class IIS restriction endonucleases encoded by the mutation linker produce blunt end cleavage. Similarly, any one linker (FIGS. 2E, 2F) can encode a combination of Class IIS endonucleases which produce blunt end and staggered end cleavage at opposite ends of the linker.

In the preferred embodiments, the mutation linker encodes random mutation nucleotides. In addition, the design of the excision and mutation linkers is such that the number of target nucleotides removed is preferably the same as the number of mutation nucleotides added so that one-for-one substitution of the target nucleotides is produced. Since in the preferred embodiments the target DNA encodes a precursor polypeptide, it is preferred that all of the target nucleotides of at least one target codon be substituted with random mutation nucleotides. In many instances, however, it is preferred that more than one target codon be so modified. In such cases, the excision and mutation linkers are chosen so that more than one adjacent codon is modified. In this regard, it is apparent by reference to Table I that use of an excision linker encoding BbvI is capable of removing a total of 12 nucleotides on each side of the insertion site (if subsequently treated with exonuclease) for a total of 24 nucleotides removed. When specifically targeted so that the insertion site is between codons, a total of eight adjacent codons can be removed and substituted with 24 random mutation nucleotides contained in the mutation linker. Thus, using BbvI in the method described herein, the maximum number of adjacent codons which may be modified is eight. It is preferred, however, that one to eight adjacent target codons, more preferably two to six adjacent target codons and most preferably two to four adjacent target codons be modified in practicing the invention. Alternatively, it is preferred that the two to forty nucleotides, more preferably ten to 20 nucleotides, or most preferably 15 to 20 nucleotides be modified.

Of course, the described method could be adapted by one skilled in the art to replace greater than 24 nucleotides. Such modifications include standard methods for nucleotide removal from the cleaved insertion point prior to excision or mutation linker ligation. Those nucleotides are then replaced by random nucleotides added to the mutation linker in excess of the number removed from the target DNA by the excision linker.

As previously indicated, the target nucleotides modified by the method of the invention are determined by the integration site of the excision linker. When the insertion site is randomly distributed throughout the target DNA, potentially all of the nucleotides within the target DNA are modified. Since insertion of the excision linker will generally be only at one insertion site for any individual vector containing the target DNA, a plurality of modified target DNA is produced when practicing the invention. Of course, the vector containing the target DNA of interest will also be modified when random integration is used and not all modifications caused by the method of the invention will be made within the particular DNA of interest. Such side reactions, however, do not detract from the utility of the invention since those replication vectors containing only the modification in the target DNA retain for the most part unmodified replication and selection sequences outside of the region containing the target DNA. When randomly or semi-randomly inserting an excision linker, any method known to those skilled in the art may be used. Random insertion places the excision linker anywhere in the target DNA; thus, potentially any set of 1–24 adjacent nucleotides can be substituted with random sequences. Such random insertion methods include insertion after DNAseI cleavage of the target DNA as described by Heffron, et al., (supra) and the insertion of an excision linker after partial digestion with restriction endonuclease as described by Kwoh, et al., (supra). DNaseI cleavage leads to truly random insertion, while the Kwoh method leads to semi-random insertion. In this context, the term semi-random refers to insertion at a single cleavage site out of several encoded cleavage sites for an endonuclease or cocktail of endonucleases. The initial single cleavage is achieved by control of reaction conditions to favor only one cleavage per molecule. Transposable elements, also known as transposons, may also be used to effect excision linker insertion. For example, it has been reported that a sequence of DNA encoding transposon target repeats embedded near the ends, and not precisely on the ends, successfully integrates into DNA (Phadnis, S. H., et al., *PNAS* 86:5908–5912, 1989). This principle may be applied in the present invention whereby the excision linker encodes Class IIS recognition sequences on the ends, and also encodes transposon target repeats recessed from the ends. The mechanism of transposon insertion then effects insertion of the excision linker either randomly or at target sequence sites depending on the type of transposon target repeat used.

In many instances, the target DNA encodes a precursor polypeptide which has been previously characterized, e.g. by way of amino acid and/or nucleic acid sequence, three-dimensional crystal structure and/or other methods to provide preliminary information concerning the structure and function of that polypeptide. In such cases, it may be desirable to localize the modifications in the target DNA to those regions which encode known or putative amino acid residues which contribute to the function of the polypeptide. For example, in the case of enzymes, one or more regions comprising amino acid residues which are involved in catalysis, substrate binding and/or other properties of the enzyme such as thermal stability, cofactor binding sites and the like may be modified. In the case of polypeptides such as hormones, known or putative regions within the polypeptide which interact with specific hormone receptors may be similarly targeted for modification. The term "active site" as used herein refers to those amino acid residues which interact with the target ligand or substrate by binding or positioning the substrate or which catalyze the reaction with a substrate or which effect mechanisms secondary to ligand binding. It is to be understood that active site amino acid residues may be adjacent in sequence and/or may be separated in sequence, their respective spatial orientations being determined by the tertiary structure of the polypeptide. Thus, active site amino acids may be contained within one or more regions of the polypeptide and be encoded by one or more regions of the target DNA.

Further, a multiplicity of libraries each containing modified target DNA localized to specific amino acid residues or regions may be generated. Modified polypeptides expressed by these libraries can be used to detect changes in the interaction of the modified polypeptides with a target that normally interacts with the unmodified polypeptide as discussed in more detail hereinafter. It is to be understood that the modified polypeptides of a given library are not derived from a precursor polypeptide by modification of the precursor polypeptide per se. Rather, in general, such modified polypeptides are obtained by modifying the precursor target DNA encoding the precursor polypeptide. Modified DNA encoding such modified polypeptides is preferably derived by the methods of the invention.

When it is desirable to localize the insertion site of the excision linker, any number of methods may be used. In some instances, convenient restriction sites may be used as insertion sites to introduce the excision linker if the restriction site is located in the region to be modified. Alternatively, and preferably, the excision linker is targeted for insertion at a predetermined site utilizing the polymerase chain reaction (PCR).

In the PCR method of the invention, four PCR primers are used to generate the excision linker at a predetermined site. The first PCR primer consists of a first region encoding all or part of the first strand of the first DNA portion adjacent to and upstream from the predetermined insertion site. The first PCR primer also comprises a second region encoding a first portion of the excision linker to be used. A second PCR primer encodes all or part of the DNA upstream on the second strand of the DNA containing the first DNA portion (see FIG. 4). This second PCR primer may be within the first DNA portion or may reside in the replicable vector containing the target DNA. The DNA encoded by and between the first and second PCR primers is thereafter amplified by standard cycles of treatment with DNA polymerase and denaturation. As a consequence, that portion of the first PCR primer encoding a first portion of the excision linker is incorporated into the amplified DNA.

Similarly, third and fourth PCR primers are used to produce a second amplified DNA. The third PCR primer comprises a first region encoding all or part of the first strand of the second DNA portion of the target DNA adjacent to and downstream from the predetermined insertion site. This third PCR primer also comprises a second region encoding a second portion of the excision linker. Each of the second regions of the first and third PCR primers together encode the entire excision linker to be inserted. A fourth PCR primer is used in conjunction with the third PCR primer to form second amplified DNA. This fourth PCR primer encodes all or part of the DNA downstream on the second strand of the DNA containing the second DNA portion. As with the second PCR primer, the fourth DNA primer may encode a part of the target DNA or may reside outside of the target DNA in the replication vector. As with the amplification promoted by the first and second PCR primers, amplification with the third and fourth PCR primers amplifies the DNA encoded by and between the primers and in addition through subsequent amplification steps incorporates the second region of the third PCR primer.

The first and second amplified DNA obtained by the foregoing PCR amplifications is then ligated so that the ends of the first and second portions of the excision linker are ligated to form the first modified DNA. The first modified DNA so formed (or portion thereof depending upon the choice of second and fourth PCR primers) is used as previously described in the methods of the invention to modify the target nucleotide end regions in the first modified DNA.

Libraries of modified target DNA expressing modified polypeptides are utilized, in general, to analyze the relationship between structure and function. For example, in the preferred embodiments as set forth in the examples, target DNA encoding the antibiotic hydrolase TEM β-lactamase is used to produce modified target DNA encoding modified β-lactamase. In Example 3, a specific method is set forth for screening antibiotics against libraries of modified β-lactamases containing modifications of two or more codons in different regions of the β-lactamase. Such libraries are be made by modifying the target bla gene (SEQ ID NO: 15)encoded on any one of a number of well-known and readily available plasmids. The libraries in Example 3 were made through modification of the bla gene (SEQ ID NO: 15) encoded on pBG66, a derivative of pJ1519. In this example, the host *E. coli*, harboring plasmid containing various modified bla genes, were cultured on plates containing a higher than minimum inhibitory concentration of the antibiotic to be tested so that only those cells harboring modified β-lactamase with enhanced activity against the antibiotic survived. Plasmids encoding active modified β-lactamase were sequenced to deduce the location and nature of the mutation.

In addition, it has been determined that these β-lactamase libraries can be used to determine the susceptibility of a particular antibiotic to neutralization by wild-type mutants. In a preferred embodiment of this aspect of the invention, the libraries of random mutations produced by the method in one or more predetermined regions of the β-lactamase each contain substantially all the possible amino acid substitutions and substantially all possible combinations of those substitutions. This ensures a meaningful sampling of the possible mutations. One powerful advantage of the present invention resides in the ability to measure successful transformants which contain the mutation linker to determine the number of different colonies present in the library. The number of positive host colonies is then used to calculate the probabilities that the most and least common codon combinations are present in the library. Those amino acids which are encoded by more than one possible combination of nucleotides are statistically more likely to be encoded by random mutations than are amino acids such as tryptophan and methionine, which are encoded by only one possible combination. In this context, the term "substantially all possible substitutions" or "substantially all combinations of substitutions" refers to a calculated probability of greater than about 50% more preferably 90% and most preferably 99% that the most statistically likely substitutions and combination of substitutions (i.e., excluding tryptophan and methione) are represented in the library.

In other embodiments of this invention, libraries encoding modified polypeptides, such as hormones, may be produced and screened to determine the relationship between the structure and function of such proteins. For example, the polypeptide targeted for modification may be human growth hormone (hGH). Such modified hGHs may be contacted with a target such as the somatogenic hGH receptor or the diabetogenic hGH receptor to determine the effects, if any, of such modifications. Information gained thereby may be used to rationally design hGH analogs with specific anabolic or metabolic activity. Alternatively, the mutated hGH analogs may be tested directly for activity in cell culture or animal assays. Conversely, the targeted polypeptide may be one of the hGH receptors. In this embodiment, the mutations in the hGH receptor are screened for activity when contacted by the normal hGH ligand. Determination of the effect of amino acid and homolog segment substitution of polypeptides such as hormones and the like are discussed in PCT Publication No. WO/89-04778 published Oct. 30, 1989 incorporated herein by reference. Such methods may be similarly used to detect and analyze changes in the activity of one or more modified polypeptides as compared to the unmodified polypeptide.

The following is presented by way of example and is not to be construed as a limitation to the scope of the invention.

EXAMPLE I

Generation of Random Replacement Libraries in the β-Lactamase Gene

In brief, three to six codons were randomized as units to determine the percentage of possible amino acid combinations that were functional. The procedure was then repeated several times for different regions of the gene to obtain a global view of the regions of the protein that are important for structure and activity.

Materials and methods:

Oligonucleotides used for construction of the "excision" linkers (SEQ ID NOS:3 and 4), "mutation" linkers (SEQ ID NOS:9 and 10) (FIG. 6), primers used for DNA sequencing and primers for PCR, were custom synthesized by the oligonucleotide synthesis facility at Genentech, Inc. using standard methods. Plasmid pJ1519 (Cunningham and Wells, supra) was a gift from J. Wells. Plasmid pBG66 was used in all experiments described here It is a derivative of p J1519 created by deleting the 210 bp BglI fragment. Bacterial strains: *E. coli* strains HB101 (hsdS20 (rB⁻ mB⁻ supE44, ara14, λ⁻, galK2, lacY1, proA2, rspL20, xyl-5, mtl⁻¹, recA13, mcrA(+), mcrB(−)) was used for random library constructions and TG1 (K12, Δ[lac-pro], supE, thi, hsdDS/FtraD36, proA⁺B⁺, lacI, lacZM15) was used for assaying ampicillin resistance and for preparation of single stranded DNA.

Media and reagents:

*E. coli* strain HB101 was grown in LB medium (Miller, J. H. (1972), "Experiments i Molecular Genetics", Cold Spring Harbor, N.Y., Cold Spring Harbor Laboratory). *E. coli* strain TG1 was maintained on glucose minimal medium plates (Maniatie, T. et al., (1982), Molecular Cloning: A Laboratory Manual. (Cold Spring Harbor, N.Y., Cold Spring Harbor Laboratory)) and growth in liquid culture for single stranded DNA isolation was in M9 minimal medium and also 2× YT medium (Miller, supra). All enzymes were purchased from New England Biolabs, except calf intestinal phosphatase was obtained from Boeringer Manneheim and DNAseI was obtained from Worthington. XGAL was obtained from Clontech Laboratories, Inc.

Plasmid isolation:

Plasmid DNA was prepared from *E. coli* by the alkaline lysis procedure (Maniatis, et al., supra). The DNA was purified in cesium chloride step gradients (Garger, S. J., et al., (1983), *Biochem. Biophys. Res. Comm.*, 117:835–842). Plasmid minipreps were made from 1.5 ml culture using the alkaline-lysis protocol of Birnboim, H. C., et al., (1979), *Nucl. Acids Res.*, 7:1513–1523. Single stranded plasmid DNA was prepared for DNA sequencing as described in Maniatis, et al., supra.

DNA sequencing reactions:

The dideoxy chain termination method of DNA sequencing was applied to single stranded plasmid DNA templates. Custom synthesized oligonucleotides were used to prime synthesis from defined sites within the bla gene (SEQ ID NO: 15).

Generation of excision linker insertions in bla:

An example of the method, the blaC66 mutagenesis experiment, in which codons 72, 73, and 74 were randomized, is illustrated in FIG. 6. The plasmid used as the starting material, pBG66, does not contain any sites for BspMI, the Class IIS restriction endonuclease used in this experiment.

In the first step of the mutagenesis experiments, an excision linker containing BspMI sites at each end (FIG. 6b (SEQ ID NOS: 3 and 4)) was inserted into the bla gene (FIGS. 6a and 6c) to form a first modified bla gene (SEQ ID NOS: 7 and 8). Positioned between the two BspMI recognition sequences was an 18 bp spacer sequence which contained an EcoR1 cleavage (SEQ ID NOS: 3 and 4) site. The excision linker insertions which led to the blaC66 mutations were made by ligating the linker to plasmid which had been semi-randomly linearized by partial restriction endonuclease digestion (Kwoh, T. J. et al., (1983), *J. Mol. Appl. Genet.*, 2:191–200). In addition to bla C66 (SEQ ID NOS:17–32), this method also yielded the insertions named in bla C80, bla C86, bla C83, bla C82, bla C81, bla C84 and bla C85. See FIG. 7. The bla C14 (SEQ ID NOS:45–68), bla C1, bla C7 and bla C31 (SEQ ID NOS: 33–44) insertions were obtained after random insertion of the excision linker after DNAseI cleavage as described by Heffron et al., (1978) supra. The bla C67, bla C75, bla C76, bla C73, bla C70, bla C71 (SEQ ID NOS: 69–71) and bla C74 (SEQ ID NOS: 72) insertions were obtained by site specific insertion of the excision linker as described in Example 2. All plasmids containing an excision linker inserted by each of these methods were treated in a manner similar to the following:

Generation of random replacement libraries.

Plasmids containing the excision linker described above were purified on cesium chloride gradients. Each individual linker insertion was taken through the following procedure: 1.5 μg of linker insert containing plasmid was digested with 2 units of the restriction endonuclease BspMI in 50 mM KCl, 10 mM Tris-Cl (pH 7.5), 10 mM MgCl₂, and 100 μg/ml bovine serum albumin (BSA) in a total volume of 40 μl at 37° C. overnight (≈16 hrs.). After the digestion, 1 unit of calf intestine phosphatase (CIP) was added and the reaction incubated at 37° C. for 30 min. CIP was inactivated by incubation at 70° C. for 15 min. To the reaction mix dNTP's were then added to a concentration of 0.05 mM along with 10 units of Klenow DNA polymerase and the reaction was incubated at 15° C. for 30 min. The reaction products were then separated on a 4% acrylamide gel. The linearized plasmid was visualized after ethidium bromide staining and the band was cut from the gel and electroeluted in dialysis tubing (Maniatis, et al., supra). The eluted DNA was precipitated in ethanol and resuspended in 10 μl TE. A 50-fold molar excess of a mutation linker with random DNA at its ends (FIG. 6F) was then ligated to the total eluted plasmid DNA (≈1.2 μg) overnight at 23° C. in 10 mM Tris-HCl (pH 7.5), 5 mM MgCl₂, 1 nM ATP, 20 mM DTT, 100 μg/ml BSA and 100 units of T4 DNA ligase in a 50 μl total volume. The reaction was inactivated by incubation at 70° C. for 10 min. The reaction mix was adjusted to 150 mM NaCl and 80 units of XhoI was added. The reaction mix was incubated at 37° C. for 2 hrs. There is a XhoI site embedded in the original linker so this digestion ensures that any plasmid that did not digest with BspMI will not be included among the mutation linker inserts. The XhoI digestion was phenol:chloroform extracted, ethanol precipitated and resuspended in 4 µl TE. This DNA was used to electroporate *E. coli* HB101 using a Gene Pulser apparatus (Bio-Rad). The efficiency of transformation using this method was routinely $5 \times 10^8$ transformants per µg plasmid DNA. The transformants were selected on LB plates containing 12.5 µg/ml chloramphenicol and 100 µg/ml XGAL. The mutation linker contains a lacO site so transformants which contain a mutation linker are blue (Herrin, G. L. et al., (1984), *Gene* 32:349–353). White colonies represent recircularized plasmids without the mutation linker. This was confirmed by isolating plasmid DNA from blue and white colonies and checking for the mutation linker by restriction enzyme digests. In all experiments blue colonies constituted 95% or more of the transformants. All transformants were pooled together and plasmid DNA was isolated and purified on a cesium chloride gradient.

2 µg of pooled mutation linker containing plasmid was digested with 2 units of BspMI, under the same buffer conditions as those described above, overnight at 37° C. in 50 µl total volume. dNTPs were added to a concentration of 0.05 mM and 10 units of Klenow DNA polymerase were added and incubated at 15° C. for 30 min. The reaction was phenol:chloroform extracted, ethanol precipitated and resuspended in 10 µl TE. The digested, blunt-ended plasmid was recircularized in ligation conditions as described above. The reaction was heat inactivated at 70° C. for 10 min and adjusted to 50 mM KCl. 50 units of NruI were then added and the digest was incubated at 37° C. for 2 hrs. An NruI site was embedded in the mutation linker, therefore this digestion eliminated any mutation linker containing plasmids that were not digested by BspMI. The reaction mix was then phenol:chloroform extracted, ethanol precipitated and resuspended in 4 µl TE. The recircularized DNA was electroporated into *E. coli* HB101 and plated on LB plates containing 12.5 µg/ml chloramphenicol and 100 µg/ml XGAL. The plates contained greater than 99% white colonies in all experiments indicating the lacO portion of the mutation linker had been released, leaving mutated β-lactamase genes only the random DNA replacement. The total transformants were pooled and plasmid DNA was extracted and pruified on a cesium chloride gradient. This plasmid collection constituted the final random substitution library which encoded a large collection of random DNA in place of bla DNA.

Selection of Functional Replacement Mutants:

To select for functional replacements, the library containing random DNA over a defined region was used to transform *E. coli* strain TG1 by a $CaCl_2$ procedure (Maniatis, et al., supra). The transformation mix was plated on LB plates containing, respectively, 1 mg/ml ampicillin, 10 µg/ml ampicillin and 12.5 µg/ml chloramphenicol.

Calculations:

The bla C66 experiment (FIG. 6; Table II) will be used as an example for the calculations used.

The percent functional replacements at 10 µg/ml and 1 mg/ml ampicillin for each experiment was calculated by dividing the number of transformants on the 10 µg/ml or 1 mg/ml plates by the number of transformants using 12.5 µg/ml chloramphenicol after adjustment of the chloramphenicol number for the number of replacements containing a STOP codon. For bla C66 the probability of not having a STOP codon is $[(61/64) \times (61/64) \times (1)] = 0.9$. The 1 for the third position reflects the fact that only the first nucleotide of the codon was randomized which eliminates the possibility of a STOP codon. The adjusted number of chloramphenicol transformants for blaC66 is given by 0.9×absolute number of chloramphenicol transformants.

The conversion of the absolute percent functional replacements to the percent functional per codon was calculated by taking the $n^{th}$ root of the absolute fraction functional where n equals the number of codons randomized. For bla C66, n=2.2. The fraction reflects only one nucleotide of the third position being randomized which results in only four different amino acids being sampled, giving 4/20=0.2.

The total possible number of different amino acid sequences for a replacement experiment was calculated based on the number of different amino acids sampled at each codon randomized. For bla C66 the calculation is 20×20×4=1600 different replacement mutants possible. The factor 4 reflects partial mutagenesis of the third position.

The pool size in Table II is the number of different random substitution mutants present in the library. It is simply the number of mutation linker containing blue colonies pooled. The number of white colonies pooled after the release of the mutation linker is also important in that if it were less than the pool size above it would limit the library size. However, in all the experiments performed the number of white colonies pooled in the final step was at least three times the blue colony pool size. The probability that the pool size in each experiment was large enough to contain the most probable (i.e., Leu Leu Leu) and least probable (i.e., Trp Trp Trp) replacement mutants (TABLE II) was calculated using the Poisson distribution using the formula:

$$\text{probability} = \frac{\lambda^x e^{-\lambda}}{X!}$$

where $\lambda = np$, n=pool size, p=probability of least or most common replacement and x=number of times the sequence occurs in pool size n. For these calculations x=0. The probability that the given sequence occurs 0 times is then calculated and subtracted from 1 to give the probability that the sequence occurs one or more times in the pool.

The average percentage of functional replacements for the 66 codons mutagenized was calculated by adding the percent functional replacements per codon numbers for each of the 66 codons and dividing by 66.

TABLE II

| Sample | amino acid position | total possible replacements | pool size | prob. least common % | prob. most common % | functional 10 µg/ml AMP % | functional 1 mg/ml AMP % | functional per codon 10 µg/ml AMP % | functional per codon 1 mg/ml AMP % |
| --- | --- | --- | --- | --- | --- | --- | --- | --- | --- |
| blaC14 | 37–42 | $9.6 \times 10^6$ | $2.3 \times 10^4$ | <0.1 | 15.3 | 4.23 | 0.05 | 52.1 | 20.9 |
| blaC67 | 69–72 | $2.8 \times 10^3$ | $1.6 \times 10^4$ | 61.5 | 99.9 | 10.25 | 0.50 | 37.9 | 10.5 |
| blaC66 | 72–74 | $1.6 \times 10^3$ | $1.6 \times 10^4$ | 62.5 | 99.9 | 6.50 | 1.62 | 28.9 | 15.3 |
| blaC75 | 102–104 | $6.4 \times 10^3$ | $4.8 \times 10^3$ | 8.0 | 99.4 | 41.38 | 0.76 | 73.0 | 17.5 |

TABLE II-continued

| Sample | amino acid position | total possible replacements | pool size | prob. least common % | prob. most common % | functional 10 µg/ml AMP % | functional 1 mg/ml AMP % | functional per codon 10 µg/ml AMP % | functional per codon 1 mg/ml AMP % |
|---|---|---|---|---|---|---|---|---|---|
| blaC76 | 130–132 | $6.4 \times 10^3$ | $2.1 \times 10^4$ | 27.5 | 99.9 | 15.72 | 0.97 | 51.6 | 19.1 |
| blaC80 | 134–136 | $6.0 \times 10^3$ | $1.1 \times 10^4$ | 80.8 | 99.9 | 12.61 | 4.52 | 47.1 | 32.4 |
| blaC86 | 146–149 | $3.2 \times 10^3$ | $1.7 \times 10^5$ | 99.5 | 99.9 | 62.08 | 3.20 | 81.3 | 22.4 |
| blaC1 | 157–160 | $3.2 \times 10^4$ | $6.0 \times 10^4$ | 5.7 | 99.9 | 0.25 | 0.01 | 15.4 | 5.0 |
| blaC73 | 168–170 | $2.0 \times 10^3$ | $2.1 \times 10^4$ | 47.9 | 99.9 | 19.98 | 0.60 | 48.9 | 10.3 |
| blaC7 | 182–186 | $2.2 \times 10^5$ | $3.4 \times 10^4$ | 0.2 | 92.9 | 55.93 | 5.03 | 85.1 | 43.6 |
| blaC31 | 196–200 | $8.0 \times 10^5$ | $1.5 \times 10^4$ | <0.1 | 55.1 | 36.96 | 1.65 | 79.1 | 38.3 |
| blaC83 | 208–210 | $2.8 \times 10^3$ | $4.3 \times 10^4$ | 92.8 | 99.9 | 28.89 | 15.61 | 59.6 | 46.1 |
| blaC82 | 224–227 | $6.4 \times 10^3$ | $4.0 \times 10^4$ | 91.1 | 99.9 | 4.70 | 0.15 | 33.6 | 9.8 |
| blaC70 | 233–235 | $1.6 \times 10^3$ | $7.4 \times 10^4$ | 98.9 | 99.9 | 0.22 | 0.02 | 6.2 | 2.1 |
| blaC71 | 235–237 | $2.4 \times 10^3$ | $2.5 \times 10^5$ | 97.7 | 99.9 | 9.21 | 0.23 | 24.7 | 6.7 |
| blaC74 | 238–241 | $6.4 \times 10^3$ | $1.8 \times 10^5$ | 93.2 | 99.9 | 44.61 | 2.46 | 74.9 | 26.8 |
| blaC81 | 250–252 | $1.6 \times 10^3$ | $7.8 \times 10^3$ | 38.1 | 99.9 | 12.12 | 3.00 | 38.1 | 20.3 |
| blaC84 | 259–262 | $1.6 \times 10^3$ | $1.3 \times 10^4$ | 53.6 | 99.9 | 0.18 | 0.05 | 5.7 | 3.2 |
| blaC85 | 286–289 | $1.6 \times 10^3$ | $5.6 \times 10^2$ | 3.3 | 70.7 | 0.20 | 0.02 | 5.9 | 2.1 |

Column 1 is the name of the mutagenesis experiment.
Column 2 is the position of the mutagenized codons within the bla gene.
Column 3 is the total possible number of different amino acid sequences that could be coded by the randomized codons.
Column 4 is the number of different random replacement mutants present in the random library generated.
Columns 5 and 6 are the probabilities that the least and most probable amino acid sequences represented given the library size of the experiment.
Columns 7 and 8 are the absolute percentage of functional replacements at 10 µg/ml and 1 mg/ml ampicillin.
Columns 9 and 10 are the percentages of functional replacements at 10 µg/ml and 1 mg/ml ampicillin normalized to a per codon basis.

Evolutionary variability among Class A β-lactamases was defined as the number of different amino acids observed at that position divided by the frequency of the most prevalent amino acid (Wu, T. T., et al., (1970), *J. Exp. Med.*, 132:211–250).

Results:

In this Example, "random replacement" mutagenesis was used to examine the importance of 19 regions, comprising 66 codons, of the TEM lactamase encoding bla gene (SEQ ID NO:15). For purposes of illustration, the methods used to generate mutations at one region, blaC66, were described above. For the purposes of describing the method of analysis of the results as a whole, FIG. 7 shows the collection of modifications obtained by the various methods described in this application. Individual linker insertions into various regions of the bla gene were obtained by the three methods described above and in Example 2. The position of individual excision linker inserts was determined (or confirmed in the case of the PCR generated insertions) by DNA sequencing. Upon sequencing it was found that the inserts generated after DNAseI treatment (bla C14, bla C1, bla C7, bla C31) actually contained small deletions of bla DNA coincident with the linker insertion (FIG. 7). As described below, these experiments were modified slightly to compensate for the deleted DNA. As illustrated in FIG. 6, the next step in the procedure was to digest the plasmid containing the linker insert with BspMI.

Because of the digestion pattern of BspMI, the excision linker and small amounts of bla DNA flanking the excision linker were released upon digestion (Mormeneo, et al., supra). The cleaved DNA was then treated with Klenow DNA polymerase to create blunt-ended, linearized plasmid. The net result is an 8 bp deletion in the bla gene (FIG. 6e). To replace the deleted nucleotides with random nucleotides, a mutation linker (SEQ ID NOS: 9 and 10) was ligated to the blunt-ended DNA. This mutation linker contained 4 bp of random sequence at each end along with embedded BspMI sites and the lacO sequence. After ligation, the mix was transformed into *E. coil* using electroporation to generate the maximum number of transformants. Colonies that contained a linker were blue due to the lacO sequence binding and titrating the lacI gene product away from the chromosomal lacO site (Herrin, et al., supra). Each blue colony represented an independent random substitution mutant. All of the colonies resulting from the transformation were then pooled and the plasmid DNA was extracted. White colonies representing recircularized plasmid without a linker were included in the pool but in every experiment they made up less than 5% of the total colonies and that 5% was eliminated in the procedure. The number of blue colonies pooled indicated the complexity of the random library. It is important to know the complexity of the library in order to determine the probability that any given amino acid sequence will be included in the library. In the bla C66 experiment, there were $1.6 \times 10^3$ different amino acid substitutions possible and $1.6 \times 10^4$ blue colonies were pooled (Table II). Therefore, the probability that the least probable replacement (i.e., W W W) was represented in the library is 62.5% and the probability that the most common replacement (i.e., L L L) was present is 99.9% (Table II).

In the next step of the procedure, the pooled plasmid DNA was digested with BspMI to release the lacO section of the linker and leave the random DNA associated with the plasmid (FIG. 6H). The plasmid was then treated with Klenow DNA polymerase to generate blunt ends and DNA ligase to recircularize the plasmid. This resulted in the replacement of 8 bp of the bla gene with 8 bp of random DNA. For those inserts of the excision linker which were associated with small deletions (FIG. 7), the deletion after BspMI digestion was larger than 8 bp. This was compensated for by using a mutation linker that had an increased amount of random DNA at the ends so that after BspMI digestion the amount of random DNA remaining with the plasmid was equal to the increased deletion size. Therefore, more codons were randomized in these cases. After recircularization of the plasmid, the random library was used to transform *E. coli*. The transformation mix was then plated on, respectively, 10 µg/ml ampicillin, 1 mg/ml ampicillin and 12.5 µg/ml chloramphenicol containing agar plates. 10 µg/ml ampicillin is the minimal concentration of ampicillin that still selects for β-lactamase function. 1 mg/ml ampicillin is the maximal concentration of ampicillin on which E. coli containing a wild type copy of the bla gene on the pBG66 plasmid will grow, therefore it selects for total β-lactamase activity. The chloramphenicol plates select for the presence of the pBG66 plasmid but do not select for β-lactamase function. The use of selections at low and high concentrations of ampicillin allowed functional random substitution mutants to be subdivided into two phenotypic classes, wild type function and partial function. Nonfunctional mutants were also isolated from the chloramphenicol plates which did not select for β-lactamase function.

Catalysis of the cleavage of the β-lactam bond of ampicillin by β-lactamase requires that the enzyme fold into a precise three-dimensional structure to make the proper contacts with the antibiotic. Thus, modified enzymes that possess even minimal activity against ampicillin must retain the basic fold of β-lactamase although the structure may be destabilized to some extent. Nevertheless, the minimal function mutants encode properties that are consistent with the protein's fold. The ability of mutants selected at high ampicillin concentrations to function at a level with wild type β-lactamase suggests these mutants have a stability and ability to bind and catalyze the cleavage of ampicillin which is the same as wild type. Thus, these mutants contain truly neutral amino acid substitutions. By counting the number of transformants on each type of plate it was possible to determine the percentage of random replacement mutants which retained wild type and minimal lactamase activity. The numerator for these calculations was the number of transformants on the ampicillin plates and the denominator was the number of transformants on the chloramphenicol plates after an adjustment to account for the probability of a STOP codon being within the non-selected replacements.

The percentage of functional random substitutions was an indication of the importance of the region randomized to the structure and/or function of the protein. A large percentage of active substitutions would indicate that a wide range of different amino acids could perform the role the wild type residues have in the structure and function of the protein. In contrast, a low percentage of active substitutions would indicate that the particular region of the enzyme contributes to the protein's structure and function and requires a specific sequence of amino acids. The ability of a residue position to tolerate amino acid substitutions can be interpreted in terms of information content, which is defined as a value that decreases as the number of allowed substitutions increases (Reidhaar-Olson, et al., supra). Thus, regions which tolerate a high percentage of substitutions encode little information in terms of the protein's structure and function while regions which tolerate few substitutions are high in information content.

Percentage of Functional Replacement.

The results of the 18 mutagenesis experiments from FIG. 7 are shown in Table II. Because the number of codons randomized was not the same in each experiment and some codons were only partially randomized, the absolute percentage of functional replacements could not be compared from experiment to experiment. Therefore, the absolute percentages were normalized to represent the percent functional substitutions on a per codon basis for each mutagenesis experiment. As expected, the frequency of random replacements passing the selection was less for 1 mg/ml ampicillin than for 10 µg/ml ampicillin. The percent active substitutions for 10 µg/ml and 1 mg/ml ampicillin versus the position of the replacement experiment is plotted in FIG. 8. It can be seen that a surprisingly large fraction of replacements were functional. For the minimal selection, the percent of functional replacements per codon varied from 5.7% for blaC84 to 85.1% for blaC7. The average percentage of replacements active at 10 µg/ml ampicillin for the 66 codons mutagenized in the experiments was 48%. This translates to approximately (20×0.48)=9.6 different amino acids, on average, being able to replace the wild type amino acid at each residue position and still retain the β-lactamase fold. This number should be regarded as the number of different amino acids able to function at a residue position if the rest of the protein retains the wild type sequence since combining substitutions, each of which individually reduces the activity of the protein somewhat, will likely result in a protein that is inactive. Nevertheless, the number suggests that the fold of the β-lactamase protein is very tolerant to mutations.

For the 1 mg/ml ampicillin selection, the percent of functional replacements per codon varied from 2.1% for bla C70 and bla C85 to 46.1% for bla C83. The average percentage of active replacements for the 66 codons mutagenized was 20 which translates to approximately (20×0.2)=4 different amino acids per residue position, on average, able to function at a residue position. Since these mutants phenotypically resemble wild type these results indicated that the number of possible neutral mutations in the bla gene is extremely large.

DNA Sequence of bla mutants:

The DNA sequences of several replacement mutants from three different mutagenesis experiments were determined in order to 1) confirm that the mutagenesis technique actually resulted in the precise replacement of a section of the bla gene with random DNA sequence and 2) to obtain more detailed information on the residue position and type of sequences that are allowed in certain regions of β-lactamase. The mutagenesis method randomizes blocks of codons and determines relative importance of that block to the structure and function of the protein. However, within the block of codons it is not possible to tell how the individual positions contribute to the observed importance of the block. By DNA sequencing several functional replacements from a mutagenesis experiment and inferring the amino acid sequences it is possible to define a consensus sequence for the region and thereby identify the contributions of individual positions.

Mutants were sequenced from the bla C66, bla C31 and bla C14 mutagenesis experiments. blaC66 encompasses residue positions 72–74 (SEQ ID NO:17) (numbering scheme according to Ambler, R. P. (1980), "The structure of β-lactamases", Phil. Trans. Ry. Soc. London. Ser. B, 289:321–331). The sequence of bla C66 active mutants is presented in FIG. 9. All of the mutants sequenced contained the expected 8 bp replacement of bla DNA sequence with random DNA sequence indicating that the method worked as expected. Examination of the spectrum of allowed amino acid substitutions revealed that Lys-73 has a stringent sequence requirement. All four of the mutants functional at 1 mg/ml ampicillin and twelve of fourteen of the 10 µg/ml ampicillin mutants contain a Lys at position 73. In contrast, Phe-72 and Val-74 can tolerate at least some substitutions. For example, can replace Phe 72 and be phenotypically wild type. Similarly, Leu can replace Val-74 with no effect. It is possible that if more 1 mg/ml replacements were sequenced other substitutions would be identified. The partial function mutants varied widely at position 72 with at least eleven different amino acids that were consistent with minimal function. Position 74 also varied but it should be noted that since only the first nucleotide in the codon was randomized Val, Leu, Ile and Phe are the only possible replacements. The results suggest that of those 4 possibilities only Phe is not allowed at position 74.

An examination of the three-dimensional structure of Class A β-lactamases suggests an explanation for the bla C66 replacement results. Although the X-ray structure of the TEM β-lactamase is not yet known to a useful resolution (Knox, J. R., et al., (1976), *J. Mol. Appl. Genet.*, 2:191–200), the TEM mutants were analyzed by examining the homologous Class A structure from *B. licheniformis* (Moews, P. C., et al., (1990), *Proteins Struc. Funct. Genet.*, 7:156–171). The assumption that Class A β-lactamases adopt a similar fold is supported by sequence homology (Ambler, supra; Boissinot, M., et al., (1990), *J. Biol. Chem.*, 265:1225–1230) and a comparison of x-ray structures of the structures of *B. licheniformis* and *S. aureus* Class A enzymes (2.5 Å resolution) (Hertzberg, et al., supra). The RMS α-carbon difference for the structures is 1.3 Å (Moews, et al., supra). Therefore, it seems a reasonable assumption that the fold of TEM β-lactamase is similar to other Class A enzymes.

In the *B. licheniformis* structure, Lys-73 is located in the active site region with it's side chain ammonium group directed into the substrate binding pocket, within hydrogen bonding distance of the catalytic Ser-70 (Moews, et al., supra). It has been suggested that Lys-73 plays a direct role in catalysis by facilitating proton transfer from the catalytic Ser-70 to the β-lactam ring nitrogen. Although the random replacement results do not address the role of Lys-73 they are consistent with a role requiring a side chain with very specific chemical characteristics.

Phe-72 and Val-74, although in the vicinity of the active site, have their side chains oriented away from the binding pocket and into the body of the protein suggesting they contribute to the structure of the enzyme. The buried nature of the side chains provides a possible explanation for the hydrophobicity of the wild type sequences and the replacement mutants with wild type function. The conservation of hydrophobicity among substitutions at buried positions has been documented for the λ repressor protein (Reidhaar-Olson, et al., supra).

It is of interest to correlate the tolerance of the residue positions to substitutions with the evolutionary conservation of sequence identity at those positions. Lys-73 is one of 28 amino acid positions which are invariant in known sequences of Class A β-lactamases (Ambler supra; Boissinot, et al., supra). The evolutionary conservation of Lys-73 is mimicked by the directed evolution of the random replacement experiment. For the Phe-72 position there are five different amino acids and for the Val-74 position there are four different amino acids among the eleven Class A lactamase sequences indicating these positions are not strongly conserved by evolution. At these positions the lack of strong evolutionary conservation is mimicked by the variation in functional random replacements.

The sequence of bla C31 active replacement mutants (SEQ ID NOS:34–44) is presented in FIG. 10. bla C31 encompasses residue positions 196–200. As listed in Table II, the percentage of functional replacements per codon for bla C31 is very high, with 79.1% of the mutants functioning at 10 μg/ml and 38.3% functioning at 1 mg/ml ampicillin. These results suggest that β-lactamase can tolerate a wide range of substitutions in the 196–200 region. The sequencing results support this conclusion. None of the residue positions are strongly conserved among either the 1 mg/ml or the 10 μg/ml ampicillin selected mutants. The functional replacements for Gly-196 are biased towards small side chains suggesting that side chain volume is important here. However, the first nucleotide of codon 196 was not mutagenized which limits the possible replacements to Gly, Ala, Val, Asp and Glu which weakens this argument. The mutant replacements for Glu-197 and Leu-198 exhibit no obvious conservation of amino acid type suggesting these positions do not require a specific sequence to perform their role in structure and/or activity. The mutant replacements with wild type levels of activity at Leu-199 appear to be biased towards large hydrophobic groups. The exception is Arg in mutant MC-8. There is no strong sequence conservation among the 10 μg/ml replacements. The mutant replacements with wild type phenotypes at Thr-200 seem to be biased towards a volume similar to that of threonine suggesting a size constraint. The 10 μg/ml mutants do not exhibit the constraint. Residues 196–200 make up a medium-sized loop connecting two α-helices in the related *B. licheniformis* structure (Moews, et al., supra). Tramontano, A., et al., (1989), *Proteins Struc. Funct. Genet.*, 6:382–394, have defined the major determinant of the structure of an extended loop, such as the 196–200 loop, as the packing of a particular residue against the rest of the protein. Leu-199 appears to perform this function in the *B. licheniformis* protein. Interestingly, Leu-199 is conserved in all eleven Class A enzymes (Boissinot, et al., supra). This may explain why there is a bias towards large hydrophobic residues among mutants at position 199. However, taken as a whole, the replacement results for residues 196–200 suggest that there are few sequence requirements to form a medium-sized loop. This suggests that the major driving force for the formation of these loops comes from outside of the loop, in effect "forcing" the region to assume the loop conformation. The random replacement results correlate well with the evolutionary conservation of positions 196–200. Positions 196, 197, 198 and 200 are not conserved among the eleven Class A sequences (Boissinot, et al., supra). These positions could also tolerate amino acid substitutions in the replacement experiments. Leu-199, however, is completely invariant among Class A sequences. In contrast to Lys-73 which is invariant and also strongly favored by random replacement, Leu-199 could tolerate a number of substitutions and retain wild type levels of activity.

The sequences of blaC14 active replacement mutants (SEQ ID NOS: 46–61) are presented in FIG. 11. bla C14 encompasses residue positions 37–42. As with bla C31, the percentage of functional replacements per codon for blaC14 is high, with 52.1% of the mutants functioning at 10 μg/ml and 20.9% functioning at 1 mg/ml ampicillin. This suggests the enzyme can tolerate a wide range of substitutions in the 37 to 42 region. This conclusion is supported by the sequences in FIG. 11. Note that position 37 is strongly biased because only one nucleotide of the codon is randomized so only four amino acids are sampled. Position 42 is also biased but twelve different amino acids can be sampled. It is apparent that there is no strong sequence conservation at any position among the mutants. Because of the lack of conservation, a number of inactive mutants were sequenced. Surprisingly, only Lys and Arg were found among the nonfunctional mutants at position 42. This result suggests that the only requirement at positions 37–42 to retain minimal β-lactamase activity is not to have Lys or Arg at position 42.

Residues 37–39 are part of an α-helix and residues 40–42 are in a turn leading to a strand of α-sheet in the *B. licheniformis* structure. Ala-42 is conserved in the *B. licheni-*

*formis* enzyme with it's side chain directed into the body of the protein in a buried position. It is not possible to introduce Lys or Arg into position 42 of the *B. licheniformis* structure without making large adjustments. This suggests there is not space in the protein to accommodate the long, charged side chains of Lys and Arg.

Glu-37 and Ala-42 are conserved among Class A lactamases. Glu-37 is invariant and only Gly is found to replace Ala-42 in the eleven Class A enzymes. Similar to the situation with Leu-199, Glu-37 and Ala-42 are examples of evolutionarily conserved residues that vary in the random replacement experiment. Glu-37 can be replaced by Ala and Ala-42 can be replaced by Gln and Ser and still retain wild type levels of activity. Positions 38 to 41 are not conserved among the Class A family and are also free to vary in the random replacement experiment.

Natural Selection vs. Random Replacement:

Because of the result that not all evolutionarily conserved residues are conserved in the random replacement experiments we decided to try to correlate the percent functional results with the evolutionary variability of the regions mutagenized. The results of the comparisons are shown in FIG. 12. The variability data was compiled for the 11 Class A β-lactamases by the method of Wu, et al., supra. Since the mutagenesis experiments randomize codons in blocks it was necessary to add the individual evolutionary variability measurements for the members of a block and divide by the total positions to obtain an average variability over the region being compared. The numbers from percent function versus average genetic variability cannot be directly compared because of different measurement units but the relative levels of variability can be compared. For example, the variability measurements are very similar for positions 37–42, 69–71, 72–74, 102–104, 146–148, 157–160, 168–171, 196–200, 208–210, 224–227, 233–235, 235–238, 238–241 and 250–252. However, several variability measurements do not correlate well. These include 130–132, 134–137, 182–184, 260–262 and 287–289. In contrast to the sequencing results, the discrepancies are not always the result of greater variability among the random replacement mutants. Regions 260–262 and 287–289 are not strongly conserved by evolution and yet very few functional substitutions were tolerated in the random replacement experiments. However, regions 130–132, 134–136 and 182–184 have a higher percentage of functional substitutions in the mutagenesis experiments than expected based on the strong evolutionary conservation of the sequences. These results emphasize the danger of assuming that the degree of evolutionary conservation of a residue is always an accurate indicator of functional importance.

EXAMPLE II

Production of Active-Site Libraries by PCR Excision Linker Insertion

Eight different plasmid libraries were generated, each of which had three codons of the bla gene DNA sequence randomized. Of the nine libraries identified in FIG. 13, one, bla C66, was generated as described in Example 1. The remaining 8 libraries were produced by a modification of the technique described in Example 1 whereby mutations were generated at predetermined sites. This was accomplished by introducing the excision linker as follows:

The target bla gene was contained in the pBG66 plasmid as described in Example 1. The excision linker had the same DNA sequence as that described in Example 1, but the insertion of the excision linker into target DNA was accomplished by site-directed polymerase chain reaction (PCR) linker insertion (FIG. 5). Two PCR primers were synthesized which were homologous to opposite strands of the targeted gene with their 5' ends at the same nucleotide position (primer a in FIG. 5b and primer c in FIG. 5d). This position defined the insertion point of the linker to be synthesized from those primers. At the 5' end of primers a and c was a "tail" each of which encoded one-half of one strand of the linker to be inserted (FIG. 5b, d). In this figure the label "BspMI" stands for the recognition sequence for the type IIS restriction endonuclease used in this experiment. A second set of PCR primers were paired with the first set, one for each of the "tailed" primers (primers b and d in FIGS. 5b and 5d). These primers matched nucleotide sequences on either end of the targeted gene and were used in conjunction with the "tailed" primers in the PCR reactions to synthesize two DNA fragments (FIGS. 5c and 5e). One end of each fragment encoded one-half of the linker to be inserted. The other end encoded a restriction/cleavage site for either NdeI or EcoR1 which lie 5' and 3', respectively, of the bla gene (FIGS. 5c and 5e). Thus, the two PCR fragments overlapped the 5' and 3' ends of the target gene, respectively. Digestion of the PCR fragments with EcoR1 and NdeI was then performed and the fragments were gel purified (Maniatis, et al., supra). The plasmid containing the bla gene was also digested with EcoR1 and NdeI and the vector fragment was gel purified (Maniatis, et al., supra). A 3-way ligation between the cleaved plasmid fragment and the amplified PCR DNA fragments was then performed to form complete target DNA vector with the excision linker at predetermined positions depending upon the choice of PCR primers (FIG. 5G). The subsequent steps in the generation of libraries were identical to Example I.

EXAMPLE III

Screening of TEM-1 β-Lactamase Active Site Libraries for Potential β-Lactam Antibiotics Bacterial pathogens acquire resistance to a specific antibiotic through production of β-lactamases that hydrolyze the amide bond in the β-lactam ring of the antibiotic to form an ineffective antimicrobial agent. In this example, a screening system was devised to screen a potential drug against every possible single amino acid substitution and also a subset of the possible double and triple amino acid substitutions in the active site of TEM-1 β-lactamase (bla gene (SEQ ID NO: 15)).

By generating nine different libraries (the bla C66 library from Example I and the 8 libraries from Example II) it was possible to randomize every amino acid residue in the active site region at least once (FIG. 13). The decision as to whether a particular residue was in the active site was based on the three-dimensional X-ray structures of the homologous class A β-lactamases from *S. aureus* and *B. licheniformis* (Hertzberg, et al., supra; Moews, et al., supra). Twenty-four residues from 5 non-contiguous regions which line the active site pocket were randomized. The location of the residues mutagenized in the random libraries are shown on the homologous *S. aureus* structure in FIG. 14. The probability that each of the nine random libraries code for all possible amino acid substitutions for the region each covers is given in Table II (supra).

Six antibiotics were chosen to test the predictive abilities of the random libraries. Mutations in the active site of TEM-1 β-lactamase exist that result in increased drug resistance phenotypes for the β-lactam antibiotics cefotaxin (Sougakoff, W. et al. (1989), *Gene*, 78:339–348; Collatz, E., et al., (1989), *Gene*, 78:349–354), cephalosporin C (Hall, A., et al., (1976), *Nature*, 318:478–480), and cephalothin. These drugs were chosen as a test of the system since if the libraries have predictive value they should minimally be able to identify previously characterized substrate specificity mutations. In contrast, cephalexin and cefoxitin were chosen for testing because no TEM-1 mutations are known to result in increased activity towards them even though the drugs have been in clinical use for some time. This suggests that these drugs are insensitive to β-lactamase mutations. This hypothesis was tested directly with the random libraries. Finally, the penicillin ampicillin was included in the screening as a control.

The screening experiments were done by first determining the minimum inhibitory concentration of each antibiotic against *E. coli* strain TG1 harboring a plasmid containing the bla gene. For all the drugs except ampicillin, agar plates were made containing a concentration of antibiotic slightly higher than the minimum inhibitory concentration so *E. coli* containing wild type TEM-1 β-lactamase would not survive. Each random library was then transformed into *E. coli* and plated on agar plates containing antibiotic. Because of the selection, only those mutants with enhanced activity against the antibiotic being tested survived. Survivors of a particular antibiotic selection were then tested for growth on the other antibiotics being screened to determine if the mutants had enhanced activity against the other antibiotics as well. The mutants were also tested against the minimum, inhibitory concentration of ampicillin. Because ampicillin is already an excellent substrate for TEM-1 β-lactamase, ampicillin was used for comparison to determine if the mutants which gain activity against the cephalosporins or cefoxitin retain high activity against ampicillin. All mutants were also tested against 10 ug/ml ampicillin to determine if they retain minimal activity against ampicillin.

The results of the screening experiment are presented in Table III.

TABLE III

| Library | 10 amp | 1mg[a] amp | cmp[b] | cefox | cephC | cphal | cftx | cplx |
|---|---|---|---|---|---|---|---|---|
| TEM-1 | + | + | + | – | – | – | – | – |
| blaC71 | + | – | + | – | + | – | – | – |
| blaC71 | + | – | + | – | + | + | – | – |
| blaC74 | + | + | + | – | – | + | – | – |
| blaC75 | | | | | | | | |
| blaC74 | + | + | + | – | – | – | + | – |
| blaC75 | | | | | | | | |
| blaC74 | + | + | + | – | – | + | + | – |
| blaC75 | | | | | | | | |
| blaC74 | + | – | + | – | – | + | – | – |
| blaC75 | | | | | | | | |
| blaC74 | + | – | + | – | – | – | + | – |
| blaC75 | | | | | | | | |
| blaC74 | + | – | + | – | – | + | + | – |
| blaC75 | | | | | | | | |

Phenotypic classes of mutants derived from the active-site libraries with enhanced activity towards β-lactam antibiotics.
[a]) Antibiotic abbreviations and concentrations: 10 amp, 10 µg/ml ampicillin; 1 mg/ml ampicillin; cmp, 12.5 µg/ml chloramphenicol; cefox, 5 µg/ml cefoxitin; cephC, 100 µg/ml cephalosporin C; cphal, 20 µg/ml cephalothin; cftx, .05 µg/ml cefotaxime.
[b]) The active-site libraries are on a plasmid, pBG66 which contains the chloramphenicol resistance gene in addition to bla. All mutants were tested to ensure they contained this marker, indicating the plasmid was present. "+" indicates library survived indicated antibiotic "–" indicates antibiotic was effective against the library.

Eight classes of specificity mutants with distinct substrate profiles were discovered in five different libraries. As expected, the libraries contained mutants with increased activity against cefotaxime, cephalosporin C and cephalothin. This result strongly supported the assertion that the libraries have predictive ability. Also, consistent with the lack of previously identified mutants, the libraries did not contain mutants with increased activity against cephalexin or cefoxitin.

The results suggested that the mutant phenotypic classes identified were due to specific interactions. For example, three random libraries did not contain any mutants which had enhanced activity against the tested antibiotics indicating that a only a limited subset of residues can alter the enzyme specificity towards the antibiotics. In addition, each mutant class had altered activity against only one or two antibiotics. If a non-specific effect, such as increased stability of the enzyme, were responsible for the phenotypes activity would be expected to increase against several antibiotics simultaneously.

Because the random libraries were in defined positions, the residue position of a new specificity mutation was immediately known to within a three amino acid window. Therefore it is known that amino acid substitutions between positions 235–237 can result in increased cephalosporin C resistance, substitutions between positions 102–104 and 238–241 can result in increased cefotaxime resistance and substitutions in all of the above region can create increased cephalothin resistance.

To identify the precise nature of the mutations conferring enhanced activity towards the antibiotics, plasmid DNA was recovered from representative members of each phenotypic class and the DNA sequence of the appropriate three codons was determined. The sequence of mutants from the blaC71 library (SEQ ID NOS: 70–71) with increased activity towards cephalosporin C and cephalothin are shown in FIG. 15. The increased activity was due to substitutions at Ala-237 of the TEM-1 enzyme. This is the same position at which mutants with increased activity towards cephalosporin C and cephalothin were previously identified (Hall, et al., supra. The fact that only the blaC71 library contained mutants with enhanced cephalosporin C activity suggested that only substitutions at Ala-237 could increase activity against the drug.

Several cefotaxime resistant mutants from the blaC74 library were sequenced (FIG. 16) (SEQ ID NOS: 73–86). Glu-240 and Arg-241 tolerated a wide range of different amino acid substitutions and there was no correlation between the substitutions and the observed phenotypes. However, there was a strong correlation between substitutions and phenotype at Gly-238. Seven different cefotaxime resistant mutants were sequenced and all contained either serine or cysteine in place of glycine. The correlation is strengthened by the finding that mutants with both high (1 mg/ml) and minimal (10 µg/ml) resistance to ampicillin but no resistance to cefotaxime did not contain serine or cystein at position 238 (FIG. 16). Serine for glycine at position 238 was also observed among clinical isolates of the TEM enzyme with increased resistance to cefotaxime (Sougakoff, W., et al., (1988), *FEBS Microbiol. Lett.*, 56:343–348; Sougakoff, et al., supra). This again emphasized the ability of the libraries to predict the sensitivity of β-lactam antibiotics to β-lactamase mutations in that the libraries predicted resistance to cefotaxime due to mutations at position 238, as had been observed among clinical isolates.

Sequencing of cefotaxime resistant mutants from the blaC75 (positions 2–104) library is in progress. A clinical isolate with increased resistance to cefotaxime has been isolated that has a lysine substitution at Glu-104 of the TEM enzyme. This substitution is likely to appear among the mutants with increased cefotaxime resistance identified in the bla C75 library. This finding suggests that clinical isolates with substitutions in the 130–132 region will arise upon continued use of cefotaxime. Sequencing of cephalothin resistant mutants from the bla C71, bla C74, and bla C75 libraries is also in progress.

The active-site library screen does not guarantee that an antibiotic found to be insensitive to β-lactamase mutations will remain insensitive indefinitely because the libraries do not assess the effects of all possible double and triple mutations in the active-site. Over extended periods of time multiple mutations which radically modify the active-site to provide new activities are possible. However, the system does provide a good indication of whether single amino acid substitutions, which will arise quickly after clinical introduction, can allow a β-lactamase to hydrolyze a newly introduced antibiotic. Therefore, the active-site libraries provide a powerful new tool for antibiotic design.

In addition to providing a screen for new antibiotics, the active-site libraries are capable of providing information concerning structure-activity relationships in β-lactamases. For example, here we have shown that substitutions at both Ala-237 and Gly-238 of the TEM-1 enzyme result in changes in substrate specificity. Much is known about structure-activity relationships of β-lactam antibiotics with respect to stability to hydrolysis by β-lactamase. However, relatively little is known about the chemical and structural features of the enzyme which cause it to degrade some β-lactam antibiotics and not others. By screening a large collection of chemically different β-lactam antibiotics and determining which substitutions increase activity towards the drugs, it will be possible to gain an intimate understanding of the chemical interactions important in determining susceptibility of β-lactams to degradation by β-lactamase. This information should allow the rational design of new antibiotics resistant to β-lactamases.

The foregoing description of the preferred embodiments of the present invention has been presented for purposes of illustration and description. They are not intended to be exhaustive or to limit the invention to the precise form disclosed, and many modifications and variations are possible in light of the above teaching. Such modifications and variations which may be apparent to a person skilled in the art are intended to be within the scope of this invention.

What is claimed is:

1. A method for modifying DNA comprising the steps of:
   (a) introducing a bidirectionally cleaving Class IIS excision linker into an insertion sits of an isolated target DNA to form a first modified DNA;
   (b) contacting said first modified DNA with Class IIS restriction endonuclease to cleave said first modified DNA and to remove said excision linker and one or more target nucleotides originally present in said target DNA and located on one or both sides of said insertion site to form second modified DNA having first and second ends;
   (c) ligating a bidirectionally cleaving mutation linker with said first and said second ends to form a third modified DNA, said mutation linker containing one or more mutation nucleotides on one or both ends of said mutation linker;
   (d) contacting said third modified DNA with Class IIS restriction endonuclease to remove that portion of said mutation linker not consisting of said one or more mutation nucleotides to form fourth modified DNA; and
   (e) ligating the ends of said fourth modified DNA to form modified target DNA wherein one or more nucleotides have been substituted, inserted or deleted as compared to said target DNA.

2. A method for modifying DNA comprising the steps of:
   (a) introducing an excision linker into an insertion site of an isolated target DNA to form a first modified DNA comprising a first DNA portion of said target DNA, said excision linker, and a second DNA portion of said target DNA, said excision linker comprising first and second recognition sequences for a Class IIS restriction endonuclease oriented and positioned in said excision linker such that the first and second cleavage sites for the cognate Class IIS restriction endonuclease for each of said first and said second recognition sequences are located respectively within said first and said second DNA portions, those nucleotides of said first portion located between said first cleavage site and one end of said excision linker comprising a first target nucleotide end region, and those nucleotides of said second portion located between said second cleavage site and the other end of said excision linker comprising a second target nucleotide end region;
   (b) contacting said first modified DNA with Class IIS restriction endonuclease capable of recognizing said first and said second recognition sequences to cleave said fast modified DNA at each of said first and said second cleavage sites to form a second modified DNA comprising third and fourth DNA portions comprising said first and said second portions wherein one or more target nucleotides have been removed with each of said first and said second target nucleotide end regions and said excision linker;
   (c) modifying the ends of said third and said fourth DNA portions to form modified third and fourth DNA portions, if necessary;
   (d) ligating a mutation linker to the ends of said third and fourth DNA portions or to said modified third and fourth DNA portions, if made, to form a third modified DNA, said mutation linker comprising third and fourth recognition sequences for Class IIS restriction endonuclease and first and second mutation nucleotide end regions, each mutation nucleotide region being located at an end of said mutation linker and comprising one or more mutation nucleotides, said third and said fourth recognition sequences being oriented and positioned in said mutation linker such that third and fourth cleavage sites are located within said mutation linker such that cognate Class IIS cleavage removes said first and said second mutation nucleotide end regions from said excision linker;
   (e) contacting said third modified DNA with Class IIS restriction endonuclease capable of recognizing said third and said fourth recognition sequences to cleave said third modified DNA at said third and said fourth cleavage sites to form a fourth modified DNA comprising fifth and sixth DNA portions each comprising respectively said third and said fourth portions or said modified third and fourth portions and each of said one or more mutation nucleotides of said first and said second mutation nucleotide end regions;
   f) modifying said fifth and said sixth DNA portions to form modified fifth and sixth portions, if necessary; and
   g) ligating the ends of said fifth and sixth DNA portions or said modified fifth and sixth DNA potions, if made, to form modified target DNA comprising said target DNA wherein at least one or more nucleotides adjacent to said insertion site have been substituted, inserted or deleted.

3. The method of claim 2 wherein said mutation nucleotides are predetermined.

4. The method of claim 2 wherein said mutation nucleotides are random.

5. The method of claim 4 wherein said mutation linker further comprises a marker capable of indicating the presence of said third modified DNA.

6. The method of claim 5 wherein said marker is lacO and said presence of said third modified DNA is determined by transforming host cells with said third modified DNA and measuring the number of host cell colonies containing said lacO marker.

7. The method of claim 2 wherein said introducing of said excision linker is by random integration into said target DNA.

8. The method of claim 7 wherein said mutation nucleotides are random.

9. The method of claim 2 wherein said introducing of said excision linker is at a predetermined insertion site of said target DNA.

10. The method of claim 9 wherein said mutation nucleotides are random.

11. The method of claim 9 wherein said introducing of said excision linker comprises the steps of:
    (h) contacting said first DNA portion of said target DNA with first and second PCR primers, said first PCR primer comprising a first region encoding all or part of the first strand of said first DNA portion adjacent to and upstream from said insertion site and a second region encoding a first portion of said excision linker, said second PCR primer encoding all or part of the DNA contained upstream on the second strand of the DNA containing said first DNA portion, and amplifying the DNA encoded by and between said first and second PCR primers to form first amplified DNA;

(i) contacting said second DNA portion of said target DNA with third and fourth PCR primers, said third PCR primer comprising a first region encoding all or part of the first strand of said second DNA portion of said target DNA adjacent to and downstream from said insertion site and a second region encoding a second portion of said excision linker, said second regions of said first and said third PCR primers together encoding said excision linker, said fourth PCR primer encoding all or part of the DNA contained downstream on the second strand of the DNA containing said second DNA portion and amplifying the DNA encoded by and between said third and said fourth PCR primers to form second amplified DNA; and j) ligating the ends of said first and said second amplified DNA containing said first and second portions of said excision linker to form first modified DNA.

12. The method of claim 2 wherein the number of target nucleotides removed from said target DNA by said excision linker is the same as the number of mutation nucleotides added by said mutation linker resulting in the substitution of one or more target nucleotide of said target DNA when said modified target DNA is formed.

13. The method of claim 2 wherein the number of target nucleotides removed from said target DNA is greater than the number of mutation nucleotides added by said mutation linker resulting in the deletion of one or more target nucleotides of said target DNA when said modified target DNA is formed.

14. The method of claim 2 wherein the number of target nucleotides removed from said target DNA is less than the number of mutation nucleotides added by said mutation linker resulting in the addition of one or more mutation nucleotides to said target DNA when said modified DNA is formed.

15. The method of claim 2 wherein said Class IIS restriction endonuclease of step (b) is a blunt-end endonuclease and said ligating of said mutation linker of step (d) is with the ends of said third and fourth DNA portions.

16. The method of claim 2 wherein said Class IIS endonuclease of step (e) is a blunt-end endonuclease and said ligating of step (g) is of the ends of said fifth and sixth DNA portions.

17. The method of claim 2 wherein said Class IIS restriction endonuclease of step (b) is not a blunt-end endonuclease, said modifying of step (c) comprises contacting the ends of said third and said fourth DNA portions with an exonuclease or DNA polymerase to respectively remove or fill in the single stranded DNA of said third and said fourth DNA portions to form said modified third and fourth DNA portions.

18. The method of claim 2 wherein said Class IIS restriction endonuclease of step (e) is not a blunt-end endonuclease and said modifying of step (f) comprises contacting said fifth and sixth DNA portions with an exonuclease or DNA polymerase to remove or fill in the single-stranded DNA of said fifth and sixth DNA portions to form said modified fifth and sixth DNA portions.

19. The method of claim 2 wherein said first recognition sequence of said excision linker is for a blunt end Class IIS endonuclease and said second recognition sequence is for a Class IIS endonuclease not consisting of a blunt-end endonuclease.

20. The method of claim 2 wherein said third recognition sequence of said mutation linker is for a blunt end Class IIS endonuclease and said fourth recognition sequence is for a Class IIS endonuclease not consisting of a blunt end endonuclease.

21. The method of claim 2 wherein said target DNA encodes a polypeptide.

22. The method of claim 21 wherein said polypeptide is selected from the group consisting of enzymes, proteinaceous hormones, proteinaceous receptors, structural proteins and regulatory proteins.

23. The method of claim 21 wherein said polypeptide is an enzyme.

24. The method of claim 23 wherein said enzyme is selected from the group consisting of antibiotic hydrolases, carbonyl hydrolases and phosphorylases.

25. The method of claim 23 wherein said enzyme is a β-lactamase.

26. The method of claim 25 wherein said target DNA encoding said β-lactamase is modified to substitute random mutation nucleotides within one or more adjacent codons within said target DNA.

27. The method of claim 26 wherein said modification is at a predetermined region in said target DNA.

28. The method of claim 26 wherein said modification of said one or more adjacent codons is made randomly throughout said target DNA.

29. The method of claim 21 wherein said mutation nucleotides are random and said method further comprises transforming a host cell with an expressible form of said modified target DNA to form a library capable of expressing a plurality of modified polypeptides encoded by said modified target DNA.

30. The method of claim 29 wherein said polypeptide interacts with a first target and said method further comprises contacting all or part of said modified polypeptides produced by said library with said first target to determine the interaction, if any, between said first target and one or more of said modified polypeptides and comparing the difference between the interaction of said modified polypeptides with the same interaction between said polypeptide and said target.

31. The method of claim 30 further comprising determining or deducing the amino acid sequence of said one or more modified polypeptides to provide an indication of one or more amino acid residues within said polypeptide or modified polypeptide which interacts with said first target.

32. The method of claim 30 wherein said polypeptide is a proteinaceous hormone and said first target is a receptor for said proteinaceous hormone.

33. The method of claim 32 wherein said proteinaceous hormone is human growth hormone and said receptor is a receptor for human growth hormone.

34. The method of claim 30 wherein said polypeptide is a proteinaceous hormone receptor and said target is a hormone for said proteinaceous receptor.

35. The method of claim 34 wherein said proteinaceous hormone receptor is a hormone receptor for human growth hormone and said target is human growth hormone.

36. The method of claim 29 wherein said modified target DNA encodes a plurality of modified antibiotic hydrolases and said method further comprises contacting all or part of said library with an antibiotic.

37. The method of claim 36 further comprising selecting one or more of said transformed host cells that survive said contacting.

38. The method of claim 36 wherein said modified antibiotic hydrolase is a β-lactamase.

39. The method of claim 38 wherein one or more adjacent amino acid residues in the active site of said modified β-lactamase are different from the corresponding amino acid residues present before modification of the β-lactamase.

40. The method of claim 37 further comprising determining or deducing the amino acid sequence of said modified antibiotic hydrolase contained in at least one of said selected cells to provide an indication of one or more amino acid residues within said modified antibiotic hydrolase which interact with said antibiotic.

* * * * *

UNITED STATES PATENT AND TRADEMARK OFFICE
CERTIFICATE OF CORRECTION

PATENT NO. : 5,677,153
DATED : October 14, 1997
INVENTOR(S) : Botstein et al.

It is certified that error appears in the above-identified patent and that said Letters Patent is hereby corrected as shown below:

Column 6, line 52, change "ID NO:69)" insert therefor --ID NO:72)--.

Column 17, line 37, delete "galK2" and insert therefor --galK2--.

Column 24, line 62, immediately following "For example," insert --Val--.

Column 73, line 2 of claim 38, immediately preceding "β-lactamase" insert --modified--.

Signed and Sealed this

Fifth Day of May, 1998

*Attest:*

*Attesting Officer*

BRUCE LEHMAN

Commissioner of Patents and Trademarks